US009149202B2

(12) United States Patent (10) Patent No.: US 9,149,202 B2
Morikawa et al. (45) Date of Patent: Oct. 6, 2015

(54) DEVICE, METHOD, AND PROGRAM FOR ADJUSTMENT OF HEARING AID

(75) Inventors: Koji Morikawa, Kyoto (JP); Shinobu Adachi, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 1182 days.

(21) Appl. No.: 13/085,806

(22) Filed: Apr. 13, 2011

(65) Prior Publication Data

US 2011/0188664 A1 Aug. 4, 2011

Related U.S. Application Data

(63) Continuation of application No. PCT/JP2010/004359, filed on Jul. 2, 2010.

(30) Foreign Application Priority Data

Jul. 3, 2009 (JP) .................................. 2009-159115

(51) Int. Cl.
*H04R 29/00* (2006.01)
*A61B 5/0484* (2006.01)
(Continued)

(52) U.S. Cl.
CPC ............ *A61B 5/04845* (2013.01); *H04R 25/70* (2013.01); *A61B 5/7225* (2013.01); *G10L 2021/065* (2013.01)

(58) Field of Classification Search
USPC .............. 381/58, 60, 312, 320, 314; 600/544, 600/545
See application file for complete search history.

(56) References Cited

U.S. PATENT DOCUMENTS 5,838,801 A 11/1998 Ishige et al.
6,330,339 B1 12/2001 Ishige et al.
(Continued)

FOREIGN PATENT DOCUMENTS

JP 06-105399 A 4/1994
JP 09-182193 A 7/1997
(Continued)

OTHER PUBLICATIONS

B Röder Event-related potentials during auditory and somatosensory discrimination in sighted and blind human subjects Cognitive Brain Research, vol. 4, Issue 2, pp. 77-93.*
(Continued)

*Primary Examiner* — Patricia Mallari
*Assistant Examiner* — Michael Catina
(74) *Attorney, Agent, or Firm* — Renner, Otto, Boisselle & Sklar, LLP

(57) ABSTRACT

An adjustment device for a hearing aid includes: an audio extraction section for, through an acoustic process of a collected audio signal, utilizing information of a phoneme or syllable contained in the audio signal to output time information, the time information identifying a point of uttering the phoneme or syllable; an electroencephalogram measurement section for measuring an electroencephalogram signal of a user; a determination section for determining a difficulty of hearing of the phoneme or syllable by relying on an event-related potential in the electroencephalogram signal based on the identified point of uttering the phoneme or syllable as a starting point; a phoneme identification section for, when a plurality of phonemes or syllables are determined as difficult to hear, identifying a chronologically preceding phoneme or syllable among them to be difficult to hear; and a gain adjustment section for, with respect to the phoneme or syllable identified by the phoneme identification section, determining a gain adjustment method based on a type of the phoneme or syllable, and adjusting a gain for the phoneme or syllable in accordance with the determined gain adjustment method.

10 Claims, 15 Drawing Sheets

(51) Int. Cl.
*H04R 25/00* (2006.01)
*A61B 5/00* (2006.01)
*G10L 21/06* (2013.01)

(56) References Cited

U.S. PATENT DOCUMENTS

| | | | |
|---|---|---|---|
| 2001/0049480 A1* | 12/2001 | John et al. | 600/559 |
| 2002/0039995 A1* | 4/2002 | Gao | 514/2 |
| 2005/0069162 A1* | 3/2005 | Haykin et al. | 381/312 |
| 2009/0049089 A1 | 2/2009 | Adachi et al. | |

FOREIGN PATENT DOCUMENTS

| | | |
|---|---|---|
| JP | 10-070790 A | 3/1998 |
| JP | 2002-223500 A | 8/2002 |
| JP | 2002-369281 A | 12/2002 |
| JP | 3482465 B | 10/2003 |
| JP | 2003-533258 T | 11/2003 |
| JP | 2007-202619 A | 8/2007 |
| JP | 4145507 B | 6/2008 |

OTHER PUBLICATIONS

International Search Report for International Application No. PCT/JP2010/004359 mailed Aug. 31, 2010.

Takano et al., "The Study of Auditory Recognition and Event-Related Potentials", IEICE Technical Report, vol. 96, No. 501 (MBE96 100-122), The Institute of Electronics, Information and Communication Engineers, Jan. 25, 1997, pp. 155-161 (with English Abstract).

Kazuoki Kodera, "Hochoki Fittingu No Kangaekata" or "Concept of Hearing Aid Fitting", Shindan to Chiryosha, 1999, p. 172 and an English translation.

Yo Miyata, "Shin Seirishinrigaku" or "New Physiopsychology", vol. 2, pp. 14-15 and a partial English translation.

Kaga et al., "Event-Related Potential (ERP) Manual-mainly concerning P300", Shinohara Shuppan Shinsha, 1995, p. 30 and a partial English translation.

Kazuoki Kodera, "Hocho No Shinpo to Shakaiteki Ouyou" or "Advances in Hearing Assistance and Social Applicability", Shindan to Chiryosha, 2006 pp. 67, 78, with concise explanation.

* cited by examiner

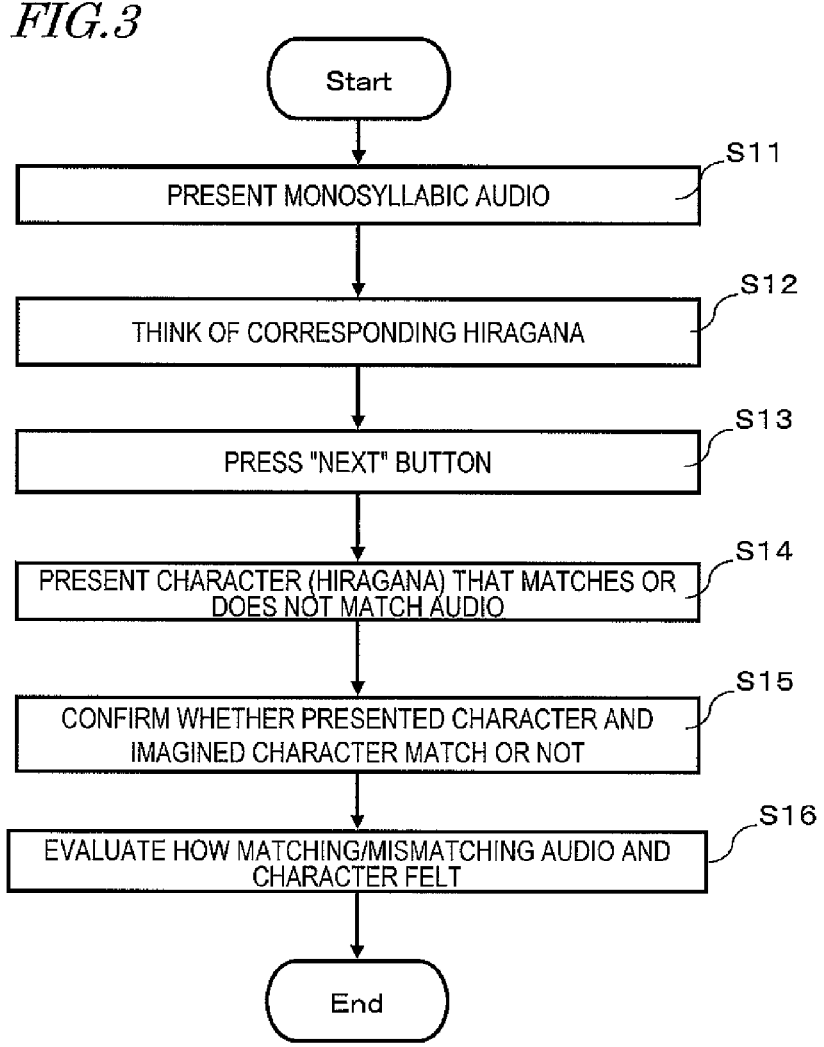
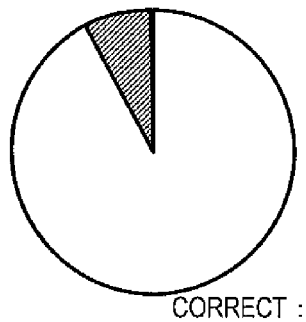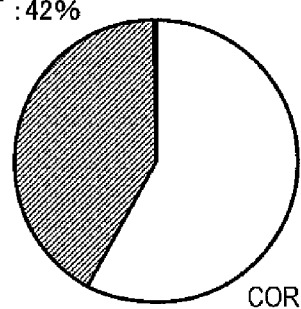
FIG.4
(a) CORRECTNESS OF BUTTON PRESSING OF TRIALS WITH HIGH CONFIDENCE OF AURAL DISTINCTION
(b) CORRECTNESS OF BUTTON PRESSING OF TRIALS WITH LOW CONFIDENCE OF AURAL DISTINCTION FIG.5   The 10-20 sysytem
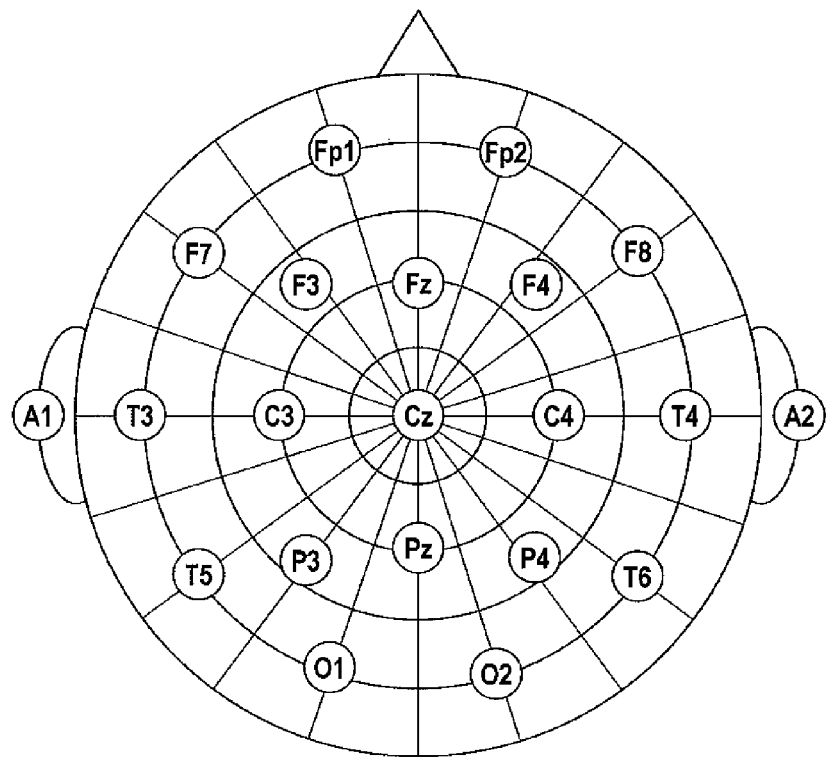
FIG.6
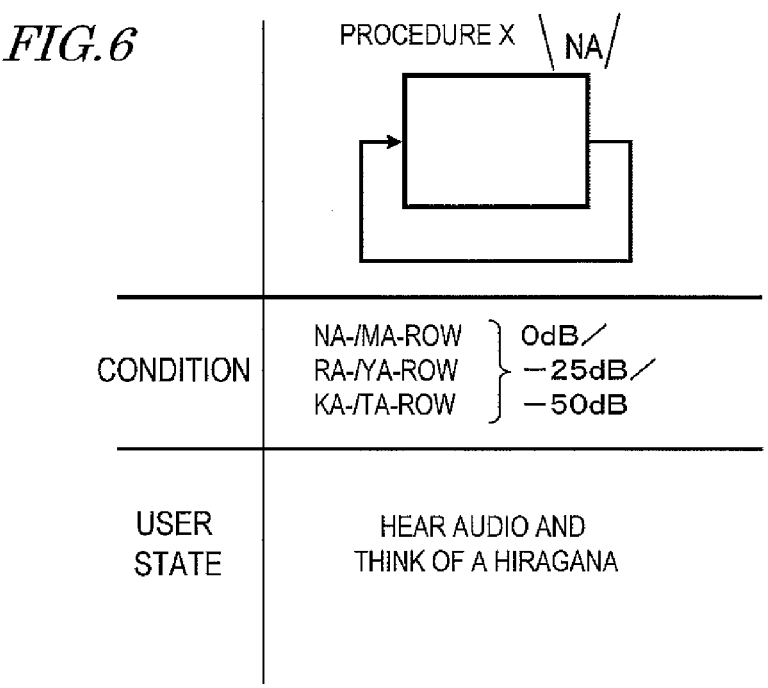

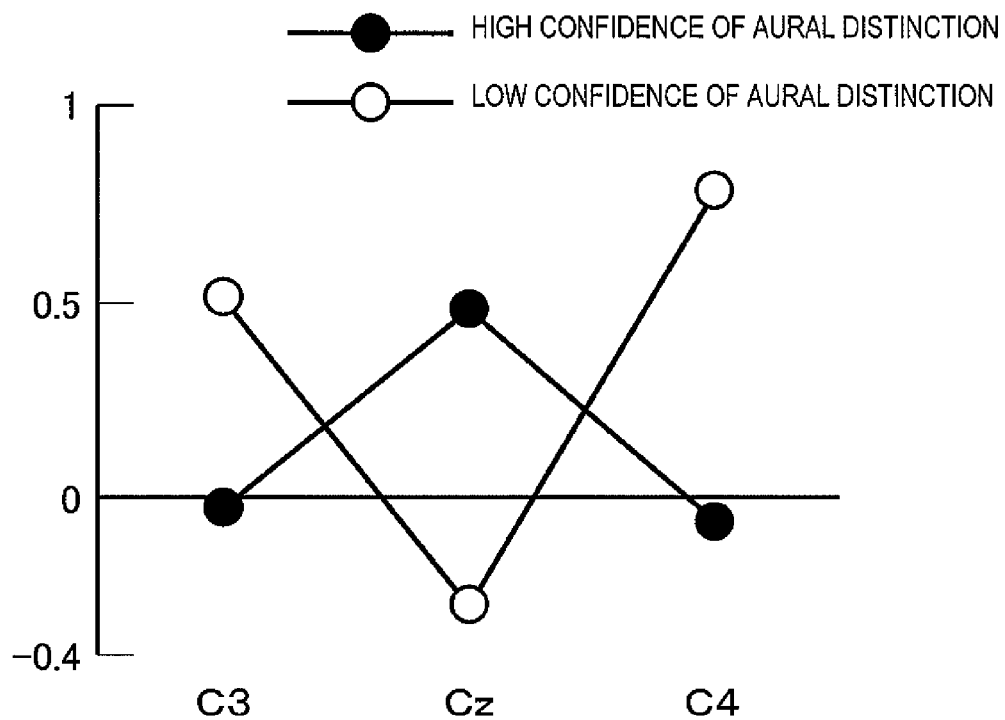

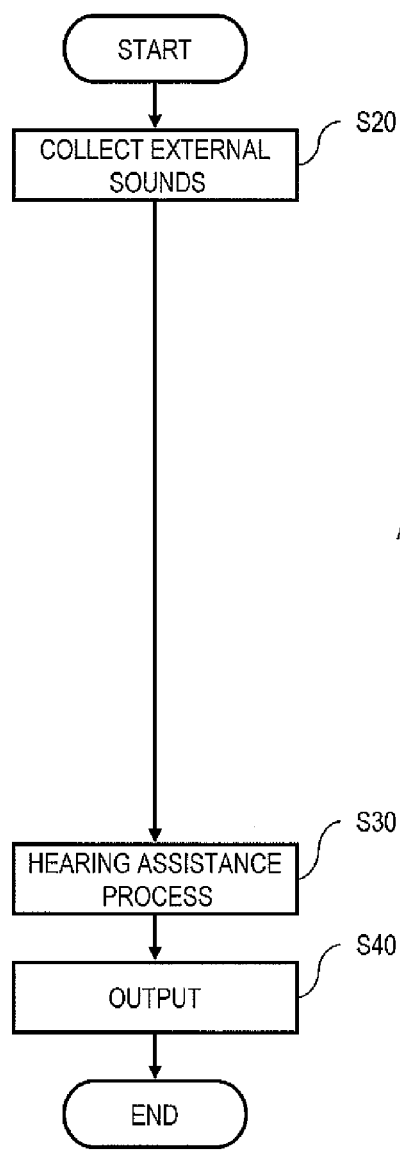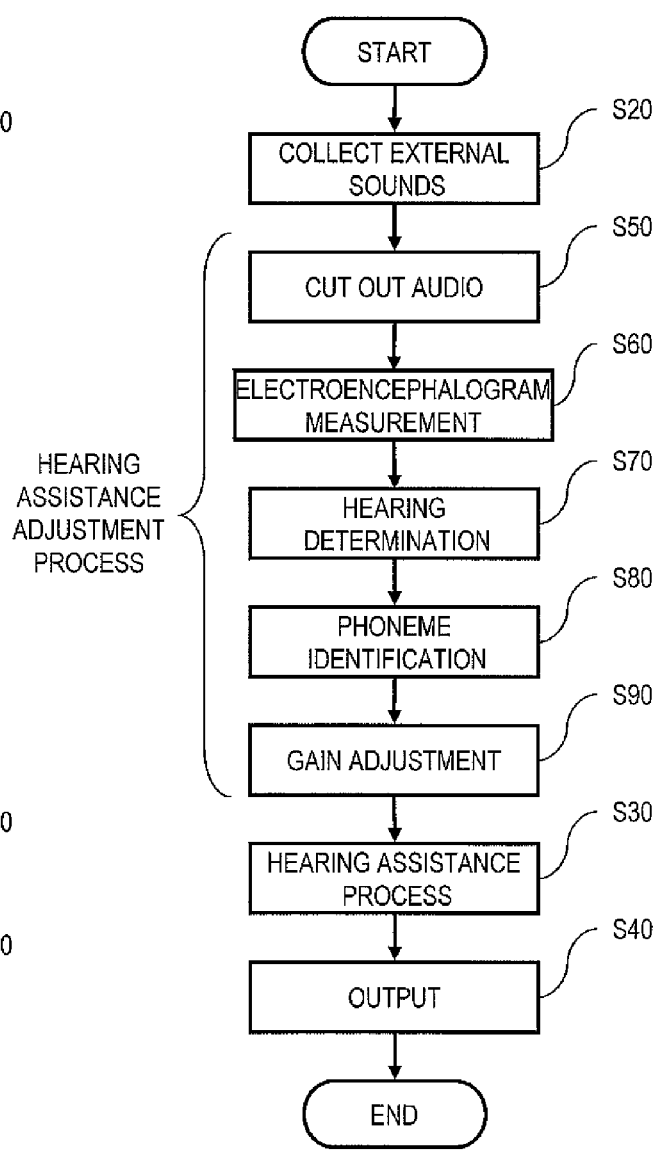

FIG.18
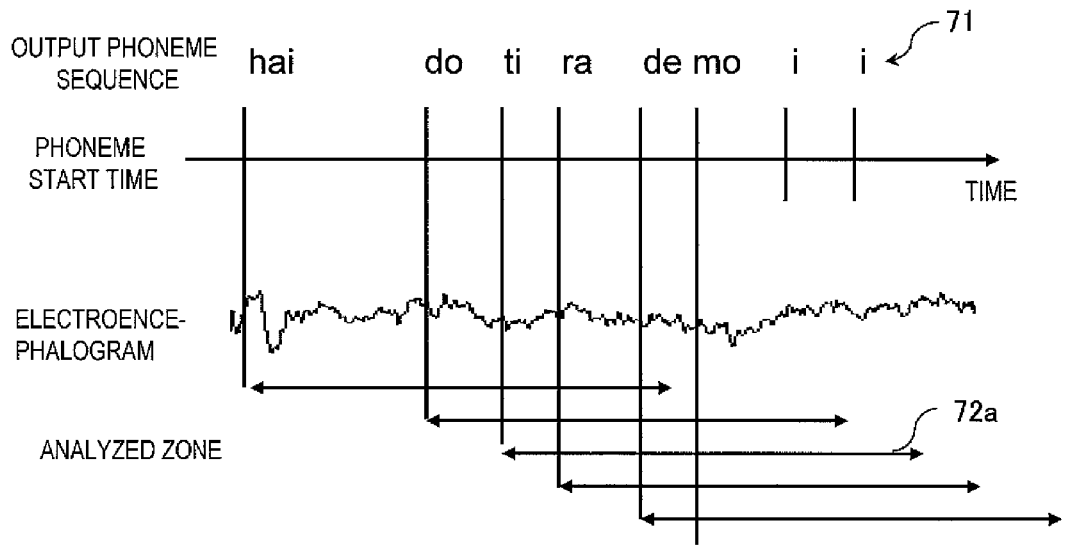
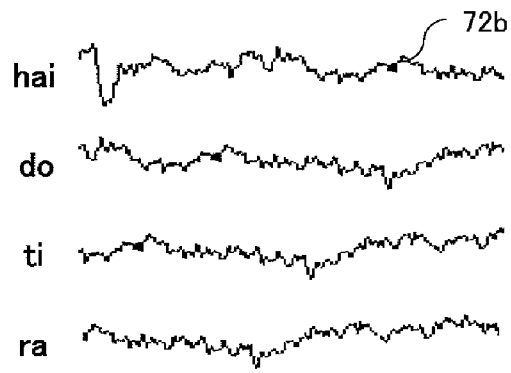
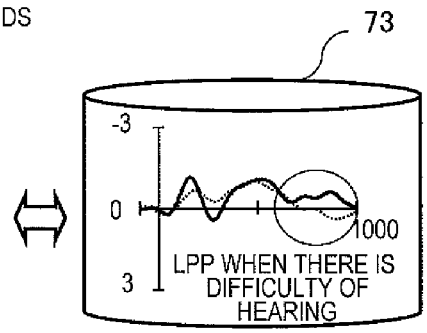
CHARACTERISTIC COMPONENT
AS TO DIFFICULTY OF HEARING
RESULT OF HEARING DETERMINATION — 77
| | hai | do | ti | ra | ... |
|---|---|---|---|---|---|
| CHARACTERISTIC COMPONENT AS TO DIFFICULTY OF HEARING | NO | YES | YES | NO | ... |

|  |  | CONSONANTS h,d,g | CONSONANTS ts,k |
|---|---|---|---|
| ADJUSTMENT METHOD | EXPANSION OF CONSONANT PORTION | EFFECTIVE |  |
|  | EXPANSION-COMPRESSION OF CONSONANT PORTION |  | EFFECTIVE |

DEVICE, METHOD, AND PROGRAM FOR ADJUSTMENT OF HEARING AID

This is a continuation of International Application No. PCT/JP2010/004359, with an international filing date of Jul. 2, 2010, which claims priority of Japanese Patent Application No. 2009-159115, filed on Jul. 3, 2009, the contents of which are hereby incorporated by reference.

BACKGROUND OF THE INVENTION

1. Field of the Invention

The present invention relates to a technique of making adjustments for a hearing aid. More specifically, the present invention relates to a technique of utilizing an electroencephalogram of a user who is wearing a hearing aid to identify phonemes which are difficult for the user to hear, and adjusting a correction process in the hearing aid to realize better hearing.

2. Description of the Related Art

In recent years, due to the aging society, increased opportunities for listening to loud music for long hours, and other influences, there is an increasing number of people suffering from presbycusis or hypacusia associated with acoustic traumas. Moreover, due to the downsizing and improved performance of hearing aids, users feel less of a psychological barrier against wearing hearing aids, and there is an increasing number of users who use hearing aids to be able to hear daily conversations more clearly.

A hearing aid is a device for compensating for the deteriorated hearing of a user through sound amplification. The amount of sound amplification which a user desires in a hearing aid depends on the level of deterioration in the hearing of the user, and on the frequency band. Therefore, before beginning use of a hearing aid, "fitting" is required for adjusting the amount of sound amplification for each frequency, in accordance with the hearing of each user.

Fitting is generally performed based on each user's audiogram. An "audiogram" is a result of evaluating how a pure tone of each frequency is heard; for example, a diagram in which, for each of a number of sounds of different frequencies, the smallest sound pressure level (decibel value) that the user can hear is plotted against frequency. An audiogram is created at a hearing aid shop or a medical institution.

A hearing aid shop or a medical institution first generates an audiogram for each user. Then, from the audiogram, an amount of amplification is determined and an initial adjustment is made according to a fitting method, which is an adjustment method for providing amplification to a sound pressure level for attaining comfortable hearing.

As necessary, a hearing aid shop further performs a speech sound intelligibility assessment, which involves presenting monosyllabic audios one by one to the user orally or from a CD, and making evaluations as to whether the speech sounds were actually heard, and thus makes a fine adjustment for the hearing aid. Through repetitions of such evaluations and hearing aid adjustments, a hearing aid is obtained which has characteristics suited to the hearing of the user.

However, there has been a problem in that satisfactory adjustments for a hearing aid may not necessarily be made even through such fully-attended adjustments, because such hearing aid evaluations and adjustments are made in a hearing aid shop and by a shop expert.

More specifically, it is in the scenes of daily life that a user of a hearing aid actually wears the hearing aid, e.g., in the household, while watching television, or while going out, and thus the optimum adjustment for the hearing aid will presumably differ from situation to situation. Conventionally, when any dissatisfaction with regard to the adjustment of a hearing aid is felt in the daily life, such scenes of dissatisfaction must be memorized (e.g., conversations are clearly heard but television tends to sound too loud; while there was no problem conversing with an expert at the hearing aid shop, talking to the family still presents a problem in aural comprehension; and so on). Then, such scenes must be conveyed to an expert at the hearing aid shop, based on which the expert makes a readjustment.

The difficulty in such adjustments is that the user needs to recall from memory those past experiences of difficulty of hearing, and try to explain the particular scene(s) and difficulty of hearing to the expert, who tries to estimate out of this dialogue what is appropriate from among a large number of adjustable items with regard to the hearing aid. In the first place, subjective expressions of hearing may permit a lot of variations, and the difficulty of adjustments is further enhanced by reliance on memory.

One solution to such problems may be an approach of making automatic readjustments in scenes of daily life. Known conventional techniques related to this approach are, in particular: a technique of making evaluations based on an objective index (such as an electroencephalogram) rather than making hearing evaluations based on oral reporting (Japanese National Phase PCT Laid-Open Publication No. 2003-533258); a technique of adjusting the reproduced sound based on changes in external ambient sounds (Japanese Patent No. 4145507); a technique of retaining a plurality of fitting parameters and switching between them (Japanese Patent No. 3482465); and so on.

The technique of Japanese National Phase PCT Laid-Open Publication No. 2003-533258 evaluates auditory characteristics for each frequency with respect to pure tones by using an electroencephalogram, based on ASSR (Auditory Steady-State Response). As a result, evaluations can be made without having to provide oral reporting, which would permit large variations from user to user.

The technique of Japanese Patent No. 4145507 ensures that music of the same sound quality is always reproduced irrespective of fluctuations in the external ambient sounds, thus being able to cope with fluctuations in the external ambient sounds to a certain extent.

The technique of Japanese Patent No. 3482465 makes use of a plurality of previously-stored fitting parameters, and switches between the fitting parameters in accordance with the acoustic environment of one's place of living.

The above techniques are techniques of adapting the hearing to the acoustic environment, which differs in each scene of life, and may be useful in making evaluations of hearing without oral reporting.

However, these techniques cannot be used to make evaluations of hearing in the daily life without inconveniencing the user, so as to realize readjustments of a hearing aid in situ. In other words, it is impossible to objectively detect a sound that is difficult for a user to hear in daily life, and make an automatic adjustment. For example, in Patent Document 1, although a user's hearing of a pure tone can be evaluated, evaluations concerning conversational sounds cannot be made. In Japanese Patent No. 4145507, although adjustments in accordance with external sounds can be made to a certain extent, no adjustments are possible that are in accordance with how the user heard them. In Japanese Patent No. 3482465, although a plurality of adjustment parameters may be retained, there is no guarantee that parameters for addressing every possible situation are provided.

For the user, the criterion as to whether or not a hearing aid needs an adjustment should be whether the user himself or herself can easily and aurally comprehend a given sound which is heard through the hearing aid, irrespective of the acoustic environment. In particular, if a phoneme that was difficult to hear can be identified, an adjustment for improving the hearing with respect to that phoneme alone can be made. Generally speaking, each individual adjustment method for hearing aids has a disadvantage in that, while it may be effective for a certain phoneme, other phonemes may be unfavorably affected by it. So long as the conventional adjustment methods are used, adjustments need to be made for every possible sound; however, such adjustments are difficult to make. Therefore, instead of the conventional adjustment methods, it would be effective to employ an adjustment method that addresses phonemes which are difficult to hear while not unfavorably affecting any other phoneme.

SUMMARY OF THE INVENTION

An objective of the present invention is to realize an adjustment device for a hearing aid which identifies the timing for making adjustments and phonemes that need improvement in hearing, without the user's need to perform any particular oral reporting or manual adjustment for various acoustic environments that are encountered in scenes of daily life, and which can automatically make readjustments.

An adjustment device for a hearing aid according to the present invention comprises: an acoustic transducer section for collecting ambient sounds and outputting an audio signal; an audio extraction section for utilizing information of a phoneme or syllable contained in the audio signal to output time information, the time information identifying a point in time of uttering the phoneme or syllable; an electroencephalogram measurement section for measuring an electroencephalogram signal of a user; a hearing determination section for determining a difficulty of hearing of the phoneme or syllable by relying on an event-related potential based on the identified point of uttering the phoneme or syllable as a starting point, the event-related potential being acquired from the electroencephalogram signal measured by the electroencephalogram measurement section; a phoneme identification section for, when a plurality of phonemes or syllables are determined by the hearing determination section as difficult to hear, identifying a chronologically preceding phoneme or syllable among the plurality of phonemes or syllables to be difficult to hear; and a gain adjustment section for, with respect to the phoneme or syllable identified by the phoneme identification section, determining a gain adjustment method based on a type of the phoneme or syllable, and adjusting a gain for the phoneme or syllable in accordance with the determined gain adjustment method.

The hearing determination section may determine the difficulty of hearing of the phoneme or syllable based on whether a predetermined characteristic component is contained in an event-related potential at 800 ms±100 ms since the point of uttering the phoneme or syllable as a starting point.

The electroencephalogram measurement section may measure the electroencephalogram signal by utilizing an electrode placed in a neighborhood of Pz of the user according to the International 10-20 system.

The hearing determination section may determine that the phoneme or syllable is difficult to hear when a positive component is contained in the event-related potential.

The electroencephalogram measurement section may measure the electroencephalogram signal by using an electrode placed in a neighborhood of Cz of the user according to the International 10-20 system.

The hearing determination section may determine that the phoneme or syllable is difficult to hear when a negative component is contained in the event-related potential.

The gain adjustment section may select one of a plurality of gain adjustment methods in accordance with the type of the phoneme identified by the phoneme identification section.

Another adjustment device according to the present invention comprises: an audio extraction section for outputting time information by utilizing information of a phoneme or syllable contained in an audio signal of an ambient sound collected by an acoustic transducer section for collecting ambient sounds, the time information identifying a point in time of uttering the phoneme or syllable; a hearing determination section for determining a difficulty of hearing of the phoneme or syllable by relying on an event-related potential based on the identified point of uttering the phoneme or syllable as a starting point, the event-related potential being acquired from an electroencephalogram signal of a user measured by an electroencephalogram measurement section for measuring the electroencephalogram signal; and a phoneme identification section for, when a plurality of phonemes or syllables are determined by the hearing determination section as difficult to hear, identifying a chronologically preceding phoneme or syllable among the plurality of phonemes or syllables to be difficult to hear, wherein the adjustment device outputs information of the phoneme identified by the phoneme identification section.

The adjustment device may output information of the phoneme identified by the phoneme identification section to a gain adjustment section for adjusting a gain for the phoneme.

A hearing assistance evaluation apparatus according to the present invention comprises: an acoustic transducer section for collecting ambient sounds and outputting an audio signal; an audio extraction section for utilizing information of a phoneme or syllable contained in the audio signal to output time information, the time information identifying a point in time of uttering the phoneme or syllable; an electroencephalogram measurement section for measuring an electroencephalogram signal of a user; a hearing determination section for determining a difficulty of hearing of the phoneme or syllable by relying on an event-related potential based on the identified point of uttering the phoneme or syllable as a starting point, the event-related potential being acquired from the electroencephalogram signal measured by the electroencephalogram measurement section; and a phoneme identification section for, when a plurality of phonemes or syllables are determined by the hearing determination section as difficult to hear, identifying a chronologically preceding phoneme or syllable among the plurality of phonemes or syllables to be difficult to hear, and accumulating the result of identification.

An adjustment method for a hearing aid according to the present invention comprises the steps of: collecting ambient sounds and outputting an audio signal; utilizing information of a phoneme or syllable contained in the audio signal to output time information, the time information identifying a point in time of uttering the phoneme or syllable; measuring an electroencephalogram signal of a user; determining a difficulty of hearing of the phoneme or syllable by relying on an event-related potential based on the identified point of uttering the phoneme or syllable as a starting point, the event-related potential being acquired from the measured electroencephalogram signal; when a plurality of phonemes or syllables are determined as difficult to hear in the determination step, identifying a chronologically preceding phoneme or syllable among the plurality of phonemes or syllables to be difficult to hear; and with respect to the identified phoneme or syllable, determining a gain adjustment method based on a type of the phoneme or syllable, and adjusting a gain for the phoneme or syllable in accordance with the determined gain adjustment method.

A computer program according to the present invention is a computer program to be executed by a computer for adjustment of a hearing aid, wherein the computer program causes the computer to execute the steps of: receiving an audio signal of a collect ambient sound; utilizing information of a phoneme or syllable contained in the audio signal to output time information, the time information identifying a point in time of uttering the phoneme or syllable; receiving a measured electroencephalogram signal of a user; determining a difficulty of hearing of the phoneme or syllable by relying on an event-related potential based on the identified point of uttering the phoneme or syllable as a starting point, the event-related potential being acquired from the electroencephalogram signal; when a plurality of phonemes or syllables are determined as difficult to hear in the determination step, identifying a chronologically preceding phoneme or syllable among the plurality of phonemes or syllables to be difficult to hear; and with respect to the identified phoneme or syllable, determining a gain adjustment method based on a type of the phoneme ox syllable, and adjusting a gain for the phoneme or syllable in accordance with the determined gain adjustment method.

According to the present invention, moments when a user wearing a hearing aid feels difficulties of hearing, as well as the relevant phonemes, are identified through electroencephalogram analysis, and the user's hearing is estimated. Based on the resultant information, an adjustment is performed which is suitable for the phonemes that have been identified as difficult to hear. It is possible to adjust a hearing assistance process in situ, i.e., in the place where the user feels any difficulty of hearing. Therefore, the user is free of the trouble of having to memorize situations where difficulties of hearing were felt and visit a hearing aid shop to offer explanations to an expert for readjustment, for example.

Other features, elements, processes, steps, characteristics and advantages of the present invention will become more apparent from the following detailed description of preferred embodiments of the present invention with reference to the attached drawings.

BRIEF DESCRIPTION OF THE DRAWINGS

FIG. 3 is a flowchart showing a procedure corresponding to one trial.

FIG. 4 is a diagram showing degrees of confidence in aural distinction of audios by participants, as categorized based on results of button pressing, and correctness/incorrectness probabilities of button pressing.

FIG. 5 is a diagram showing electrode positions according to the International 10-20 system.

FIG. 6 is a diagram showing the experimental procedure of an electroencephalogram measurement experiment in outline.

FIG. 9 is a diagram showing zone average potentials of event-related potentials from 700 ms to 900 ms at electrode positions C3, Cz, and C4, based on the point of audio presentation as a starting point, with respect to different degrees of confidence of aural distinction.

FIG. 10 is a diagram, compiled by the inventors, showing correspondence between presence or absence of a positive component and confidence of aural distinction and ease of hearing.

FIG. 14A is a diagram showing a procedure of processing which is performed only by a hearing aid.

FIG. 14B is a diagram showing in outline a combined procedure including the processing performed by the hearing aid adjustment system 100 of the present embodiment.

FIG. 18 is a diagram showing an exemplary data processing in a hearing determination process.

DETAILED DESCRIPTION OF PREFERRED EMBODIMENTS

Figure 1:
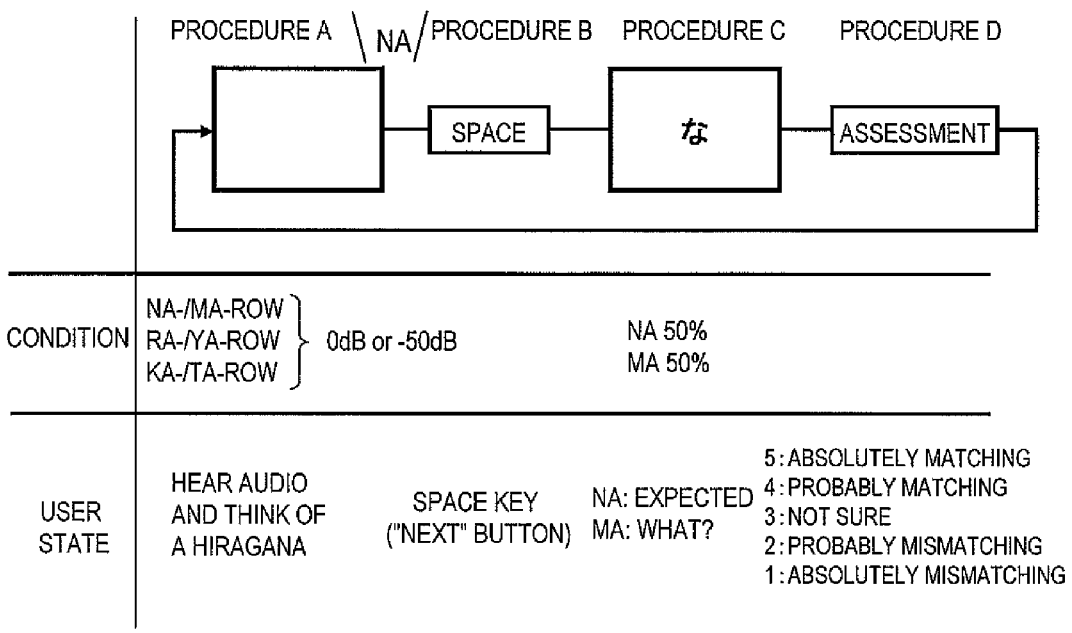
FIG. 1 is a diagram describing the experimental procedure of a behavioral experiment in outline.

Hereinafter, with reference to the attached drawings, embodiments of the "adjustment device for a hearing aid" according to the present invention will be described.

The constitution of an adjustment device for a hearing aid according to the present invention includes two technical aspects as follows. One is that an ease of hearing (confidence of aural distinction) is evaluated based on electroencephalogram measurement. The other is that, when evaluating an ease of hearing of a continuous audio based on electroencephalogram measurement, a phoneme(s) that is difficult to hear is identified.

As for the first technical aspect of evaluating confidence of aural distinction based on electroencephalogram measurement, the inventors have conducted two kinds of experiments, which the inventors have devised on their own for enabling a speech sound intelligibility assessment without requiring an answer input from a user. Then, they discovered an index which enables evaluation with respect to speech sounds, as opposed to the conventional evaluation with respect to pure tones.

Prior to the description of the embodiments, the details of the two kinds of experiments and the novel findings obtained therefrom will be described first.

Note that the second technical aspect has been envisioned by the inventors based on the results of a first experiment and on the findings from an auditory study where a plurality of speech sounds successively occur. The second technical aspect will be described in detail in the description of the embodiments.

In order to realize a speech sound intelligibility assessment which does not require oral reporting by a user, the inventors have conducted a behavioral experiment and an electroencephalogram measurement experiment as follows.

First, the inventors conducted a behavioral experiment for examining the relationship between confidence of aural distinction concerning audios and probability of confusion. Specifically, a monosyllabic speech sound(s) were presented in the form of an audio and a character (hiragana), and a user was asked to confirm whether the audio and the character were identical, who used a button to indicate his or her confidence of listening comprehension concerning the audio. This allowed the inventors to recognize the facts that the probability of confusion is as low as 10% or less when the confidence of aural distinction concerning the audio is high, and that the probability of confusion is as high as 40% or more when the confidence of aural distinction is low.

Next, the inventors conducted an electroencephalographic experiment where a monosyllabic speech sound was presented to a person in the form of an audio and his or her reaction to the audio presentation was examined. Then, based on the confidence of aural distinction acquired through the behavioral experiment, an arithmetic mean of an event-related potential, which is a signal component of the electroencephalogram, was taken. It was thus found that, when the confidence of aural distinction for the audio is high, a positive component is induced in the neighborhood of the central portion of the head at a latency from 700 ms to 900 ms in the event-related potential based on an audio stimulation as a starting point, as compared to the case where the confidence of aural distinction for the audio is low.

From the findings based on the above behavioral experiment and electroencephalographic experiment, it has been found that a confidence of aural distinction for an audio can be determined from the presence or absence of a positive component in an event-related potential near the central portion of the head at a latency from 700 ms to 900 ms based on the point of audio presentation as a starting point, and that a speech sound intelligibility corresponding thereto can be evaluated. Conventionally, a speech sound intelligibility assessment is made based only on the correctness of a user's answer, which is given orally, etc. In contrast, the present approach realizes a speech sound intelligibility assessment based on whether the user believes that he or she has aurally distinguished an audio or not, as opposed to whether an audio has actually been correctly aurally distinguished or not.

1. Behavioral Experiment

The inventors conducted a behavioral experiment in order to example the relationship between confidence of aural distinction concerning audios and probability of confusion. Hereinafter, with reference to FIG. 1 to FIG. 3, the experimental setting and experimental results of the behavioral experiment conducted will be described.

Six undergraduate or graduate students with normal hearing participated in the experiment.

FIG. 1 shows the experimental procedure of the behavioral experiment in outline.

Figure 2:
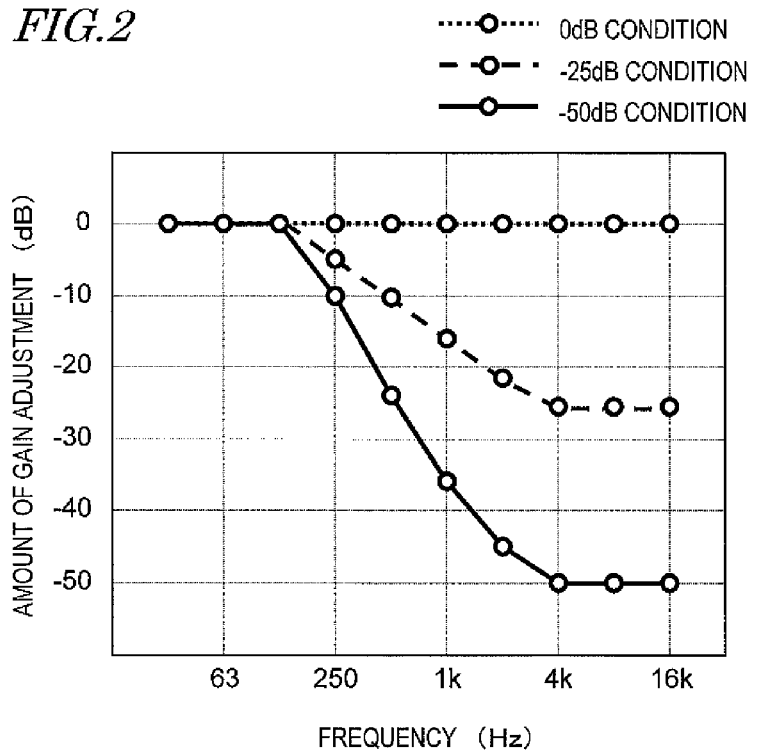
FIG. 2 is a diagram showing amounts of gain adjustment for different frequencies, corresponding to three conditions.

First, a monosyllabic audio was presented in procedure A. With reference to "HOCHOKI FITTINGU NO KANGAEKATA (or "Concept of Hearing Aid Fitting") (Kazuoki KODERA, Shindan To Chiryosha, 1999, p. 172), the stimulation speech sound was selected from among a pair of na- and ma-rows, a pair of ra- and ya-rows, and a pair of ka- and ta-rows, which are known to mutually induce mistakes in listening comprehension. Each experimental participant was instructed to think of a hiragana upon hearing the audio. Audios under the following three conditions were presented, with the frequency gain being modified so that the confidence of aural distinction would be diversified for each audio among participants with normal hearing: (1) (0 dB condition) no frequency gain modification was applied, meant as an audio that is easy to aurally distinguish; (2) (−25 dB condition) the gains for frequencies from 250 Hz to 16 kHz were gradually adjusted to −25 dB (attenuated); and (3) (−50 dB condition) the gains for frequencies from 250 Hz to 16 kHz were gradually adjusted to −50 dB (attenuated). FIG. 2 shows amounts of gain adjustment for different frequencies under conditions (1) to (3). The reason for attenuating the frequency gain for higher frequencies is to reproduce a typical pattern of hypacusia of elderly people. Elderly people suffering from hypacusia generally have difficulties in hearing sounds of higher frequencies. By attenuating the frequency gain for higher frequencies, people with normal hearing are allowed to experience a hearing which is similar to the difficult hearing of elderly people suffering from hypacusia.

Next, in procedure B, the experimental participant was asked to press the SPACE key on the keyboard. Procedure B, which concerns a button pressing for being able to proceed to procedure C, was introduced in this experiment to allow the participant to experience the character stimulation of procedure C at his or her own pace. This button is also referred to as the "NEXT" button.

In procedure C, a hiragana character was presented on a display. The character matching the audio presented in procedure A was presented as a matching trial, and a hiragana not matching the audio was presented as a mismatching trial, both with a probability of 0.5. As each mismatching hiragana, a character in a different row from that of the audio was chosen, from within a pair of na- and ma-rows, a pair of ra- and ya-rows, or a pair of ka- and ta-rows (which are generally supposed to induce many mistakes in listening comprehension), while the vowel was not changed. For example, if a hiragana "な (na)" was presented in procedure A, then "な" was to be presented as a matching trial in procedure C, and "ま (ma)" was to be presented as a mismatching trial in procedure C.

Procedure D involves a button pressing (numbers 1 to 5 on the keyboard) for confirming how mismatching the audio presented in procedure A and the character presented in procedure C were to the participant. The participant was supposed to press "5" to express "absolutely matching", to express "probably matching", "3" to express "not sure", "2" to express "probably mismatching", and "1" to express "absolutely mismatching". If 5 or 1 was pressed during this button pressing, it means that, although the participants were diversified between correct and incorrect (as a result of confusion) in procedure C, they were confident in their aural distinction at the point of hearing the audio presented in procedure A. Similarly, if any of 2 to 4 was pressed, it means that the participants were unconfident in their aural distinction of the audio.

In the experiment conducted, procedure A to procedure D described above was repeated 108 times (108 trials).

FIG. 3 is a flowchart showing a procedure corresponding to one trial. In this flowchart, for ease of explanation, the operation of the apparatus and the operation of the experimental participant are both present.

step S11 is a step of presenting a monosyllabic audio to the experimental participant. The audio was presented under the three conditions of the 0 dB condition, the −25 dB condition, and the −50 dB condition, these conditions being in random order (procedure A).

Step S12 is a step where the participant thinks of a corresponding hiragana upon hearing the monosyllabic audio. Note that a "hiragana" is a character (phonogram) representing a certain pronunciation in the Japanese language.

Step S13 is a step where the participant presses the SPACE key as a "NEXT" button (procedure B).

Step S14 is a step of presenting on a display a hiragana character matching the audio or a hiragana character mismatching the audio, both with a 50% probability as reckoned from step S13 as the starting point (procedure C).

Step S15 is a step of confirming whether the hiragana which the participant thought of at step S12 matches the hiragana presented at step S14.

Step S16 is a step of answering how matching/mismatching they were felt to the participant at step S15, via number keys of 1 to 5 (procedure D).

The experimental results of the behavioral experiment are described below.

FIG. 4 is a diagram showing degrees of confidence in aural distinction of audios by participants, as categorized based on results of button pressing, and correctness/incorrectness probabilities of button pressing. The degrees of confidence of aural distinction were categorized as follows. Any case where 5 (absolutely matching) or 1 (absolutely mismatching) was pressed was defined as a case with a "high" confidence of aural distinction. Out of all trials, the probability that the confidence was "high" was 60.4% (522 trials in 864 trials). Any case where 4 (probably matching), 3 (not sure), or 2 (probably mismatching) was pressed was defined as a case with a "low" confidence of aural distinction. Out of all trials, the probability that the confidence was "low" was 39.6% (342 trials in 864 trials). The correctness of button pressing was determined based on matching/mismatching between the audio and the character and the button that was pressed. The cases where 5 (absolutely matching) or 4 (probably matching) was pressed for a matching trial, or 1 (absolutely mismatching) or 2 (probably mismatching) for a mismatching trial were defined as "correct", whereas any other case was defined as "incorrect".

FIG. 4(a) shows correctness/incorrectness results of button pressing in trials with high confidence of aural distinction. It can be seen that the correct button is selected in almost all trials (92%). This indicates that the audio is correctly aurally-distinguished when the confidence of aural distinction is high. Based on these results, it can be said that a high speech sound intelligibility assessment may be made when the confidence of aural distinction is high.

FIG. 4(b) shows correctness/incorrectness results of button pressing in trials with low confidence of aural distinction. It can be seen that there is a high probability that the wrong button was pressed (42%). This indicates that confusion is likely to occur when the confidence of aural distinction is low. Based on these results, it can be said that a low speech sound intelligibility assessment may be made when the confidence of aural distinction is low.

Note that each participant's probability of confusion was significantly high ($p<0.01$) when the confidence of aural distinction was high.

Thus, through the behavioral experiment, a clear possibility has been indicated that speech sound intelligibility assessment can be realized based on a user's confidence of aural distinction concerning audios. Therefore, if confidence of aural distinction can be measured by a method other than button pressing, a speech sound intelligibility assessment not involving any answer inputs can be realized based on that index. Paying attention to the event-related potential of the electroencephalogram, the inventors have conducted an electroencephalogram measurement experiment to examine whether there exists an electroencephalogram component that reflects differences in confidence of aural distinction concerning audios. Hereinafter, the electroencephalogram measurement experiment that was conducted will be described.

2. Electroencephalogram Measurement Experiment

In order to examine a relationship between the confidence of aural distinction concerning audios and the event-related potential after audio presentation, the inventors have conducted an electroencephalogram measurement experiment. Hereinafter, with reference to FIG. 5 to FIG. 9, the experimental setting and experimental results of the electroencephalogram measurement experiment conducted will be described.

The experimental participants were the same six undergraduate or graduate students in the behavioral experiment.

By using electrodes placed at the Fz, Cz, Pz, C3, and C4 positions (International 10-20 system) on the scalp, the inventors measured and recorded each electroencephalogram on the basis of the right earlobe. FIG. 5 is a diagram showing the electrode positions according to the International 10-20 system. The sampling frequency was 200 Hz, and the time constant was 1 second. It was subjected to a 1 to 6 Hz digital band-pass filter off-line. As an event-related potential in response to an audio presentation, a waveform from −100 ms to 1000 ms was cut out based on the point of audio presentation as a starting point. An arithmetic mean of the event-related potential was taken based on the confidence of aural distinction with respect to each speech sound and each participant, under each condition (0 dB/−25 dB/−50 dB) in the above-described behavioral experiment.

FIG. 6 shows the experimental procedure of the electroencephalogram measurement experiment in outline.

In procedure X, a monosyllabic audio was presented. Similarly to the behavioral experiment, with reference to "HOCHOKI FITTINGU NO KANGAEKATA (or "Concept of Hearing Aid Fitting") (Kazuoki KODERA, Shindan To Chiryosha, 1999, p. 172), the stimulation speech sound was selected from among a pair of na- and ma-rows, a pair of ra- and ya-rows, and a pair of ka- and ta-rows, which are known to mutually induce mistakes in listening comprehension. Each experimental participant was instructed to think of a hiragana upon hearing the audio. Similarly to the behavioral experiment, audios under the following three conditions were presented, with the frequency gain being modified so that the confidence of aural distinction would be diversified for each audio among participants with normal hearing:

(1) (0 dB condition) no frequency gain modification was applied, meant as an audio that is easy to aurally distinguish;

(2) (−25 dB condition) the gains for frequencies from 250 Hz to 16 kHz were gradually adjusted to −25 dB (attenuated); and (3) (−50 dB condition) the gains for frequencies from 250 Hz to 16 kHz were gradually adjusted to −50 dB (attenuated).

In the experiment conducted, the above procedure X was repeated 108 times (108 trials).

Figure 7:
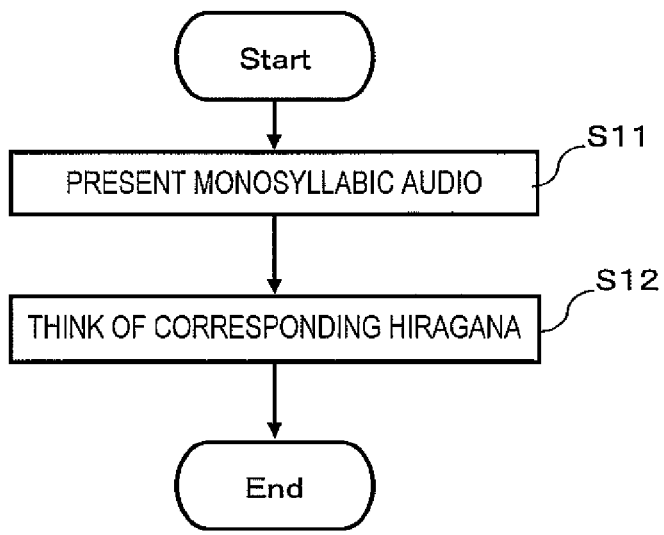
FIG. 7 is a flowchart showing a procedure corresponding to one trial.

FIG. 7 is a flowchart showing a procedure corresponding to one trial. Any block that has a like counterpart in FIG. 3 will be denoted by a like reference numeral, and the description thereof will be omitted. The difference from FIG. 3 is that step S13 to step S16 are omitted, so that each experimental participant is not required to make any explicit action.

Hereinafter, experimental results of the electroencephalogram measurement experiment will be described.

Figure 8:
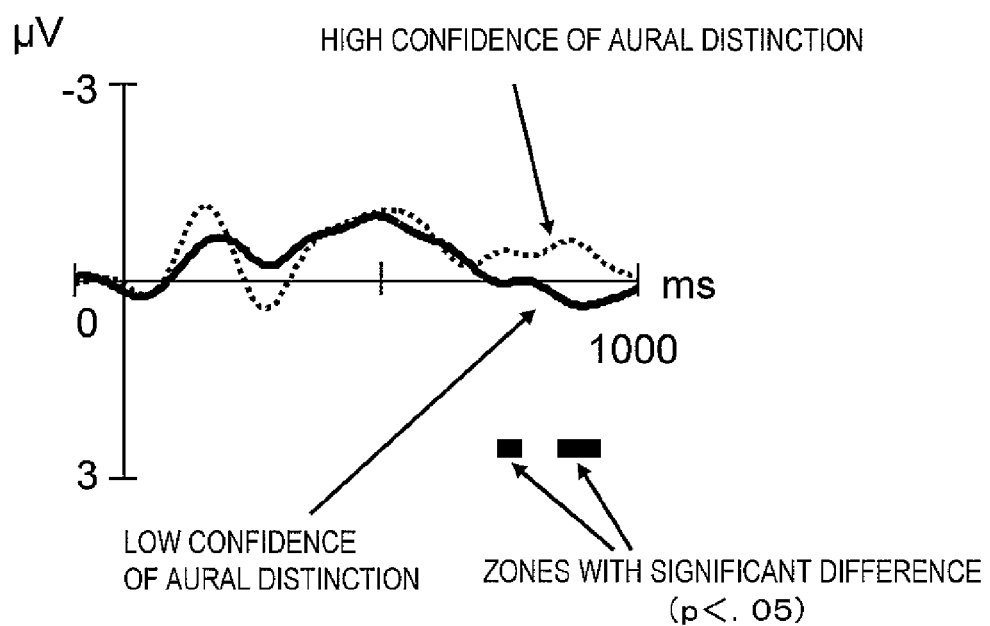
FIG. 8 is a waveform diagram showing event-related potentials at Pz, based on audio presentation as a starting point, where total arithmetic means are taken based on confidence of aural distinction.

FIG. 8 shows event-related potentials at Pz, based on audio presentation as a starting point, where total arithmetic means are taken based on confidence of aural distinction. An arithmetic mean of the event-related potential was taken based on the confidence of aural distinction with respect to each speech sound and each participant, under each condition (0 dB/−25 dB/−50 dB) in the above-described behavioral experiment. In FIG. 8, the horizontal axis represents time in units of ms, whereas the vertical axis represents potential in units of μV. As is clear from the scales shown in FIG. 8, the lower direction in the graph corresponding to plus (positive), and the upper direction corresponds to minus (negative). The baseline is set so that an average potential from −100 ms to 0 ms is zero.

In FIG. 8, the broken line represents an arithmetic mean waveform of the event-related potential at the electrode position Pz in the case where the confidence of aural distinction was high in the behavioral experiment, and the solid line represents that of the case where the confidence of aural distinction was low. It can be seen from FIG. 8 that, as compared to the broken line representing a high confidence of aural distinction, a positive component appears at a latency from 700 ms to 900 ms in the solid line representing a low confidence of aural distinction.

A zone average potential from 700 ms to 900 ms of each participant was −0.47 μV in the case of a high confidence of aural distinction, and 0.13 μV in the case of a low confidence. Through a t-test of the zone average potential, it was found that the zone average potential was significantly large in the case of a low confidence of aural distinction ($p<0.05$).

From these results, the inventors have drawn the conclusion that a positive component of an event-related potential at a latency from 700 ms to 900 ms based on the point of audio presentation as a starting point reflects confidence of aural distinction, such that the positive component can be utilized as an index of confidence of aural distinction. As a result of performing a t-test for every sampling from 0 ms to 1000 ms, the only time slots where a significant difference de to a difference in confidence of aural distinction lasted for 30 ms or more were 730 ms to 770 ms and 840 ms to 915 ms.

FIG. 9 is a diagram showing zone average potentials of event-related potentials from 700 ms to 900 ms at electrode positions C3, Cz, and C4, based on the point of audio presentation as a starting point, with respect to different degrees of confidence of aural distinction. Lines jointed by black circles shown in FIG. 9 represent a zone average potential of the case of a high confidence of aural distinction, and lines jointed by white circles represent the case of a low confidence of aural distinction. As a result of conducting a t-test of the zone average potential with respect to a high confidence and a low confidence for each of the electrode positions C3, Cz, and C4, a significant difference was found for each position ($p<0.05$).

It can be seen from FIG. 9 that, at the electrode position Cz, the event-related potential is positive in the case of a high confidence of aural distinction, and the event-related potential is negative in the case of a low confidence of aural distinction. Paying attention to the polarity of the event-related potential, it can be seen that the polarity is inverted between the measurements at the electrode position Pz (FIG. 8) and the measurements at the electrode position Cz (FIG. 9). As an event-related potential with respect to an auditory stimulation, a P300 component is generally known. The polarity would hardly be reversed between the electrode positions Cz and Pz in the P300 component. Moreover, since the latency of the component obtained in this experiment is from 700 ms to 900 ms (as opposed to the latency of the P300 component, which is near 300 ms), and so on, it is highly possible that this positive component which is induced at the electrode position Pz in the case of a low confidence of aural distinction is a distinct component from the P300 component. The following description will mainly illustrate the case of using an electroencephalogram signal which is measured at the electrode position Pz as an example. In the case where the electrode position is Cz, however, the respective polarities should read the other way around, as stated in the beginning of this paragraph. According to "SHINSEIRISHINRIGAKU (or "New Physiopsychology") Vol. 2" (supervised by Yo MIYATA, Kitaoji Shobo, 1997), page 14, the "P300 component" is generally a positive component of an event-related potential near a latency of 300 ms that is induced in response to a target stimulation in an oddball task.

Furthermore, it can be seen from FIG. 9 that, at the electrode positions C3, Cz, and C4, the lines jointed by black circles showing the zone average potential in the case of a high confidence of aural distinction and the lines jointed by white circles showing the zone average potential in the case of a low confidence of aural distinction differ in their potential distributions (relative magnitudes). As a result of multiple comparison, a significant difference was found between the potential distributions ($p<0.05$). This indicates that confidence of aural distinction can also be determined by using the potential distributions at the electrode positions C3, Cz, and C4.

The positive component at the electrode position Pz at a latency from 700 ms to 900 ms (FIG. 8) and the characteristic component at the electrode positions C3, C4, and Cz at a latency from 700 ms to 900 ms (FIG. 9) can be identified by various methods. For example, a method of applying threshold processing to the peak amplitude level near the latency of about 700 ms, a method of generating a template from a typical waveform of the aforementioned component and calculating a similarity level with that template, and the like can be used. Note that such a threshold value or template may be that of a typical user as prestored, or may be generated for each individual person.

In this experiment, each arithmetic mean was taken from about 40 summations of the data of six participants, this being in order to confirm the fact that a component which is characteristic to confidence of aural distinction is sure to appear in an event-related potential based on the point of audio presentation as a starting point. However, depending on the method of characteristic amount extraction (e.g., wavelet transformation of the waveform) or the method of identification (e.g., support vector machine learning), identification of a positive component is possible with no summations or only a small number of summations.

In the present specification, in order to define a component of an event-related potential, a point in time after the lapse of a predetermined time since a given point is expressed by referring to a "latency from 700 ms to 900 ms", for example. This means possible inclusion of a range from 700 ms to 900 ms around a specific point in time. Herein, it is to be understood that the expression "at a latency from 700 ms to 900 ms" is also exclusive of the boundaries of 700 ms and 900 ms.

Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI—(or "Event-Related Potential (ERP) Manual—mainly concerning P300—"), edited by Kimitaka KALA et al., Shinohara Shuppan Shinsha, 1995)". Therefore, the terms "about X ms" and "near X ms" mean that a breadth of 30 to 50 ms may exist before or after X ms (e.g., 300 ms±30 ms, 700 ms±50 ms).

Although the aforementioned "breadth of 30 ms to 50 ms" is a generic example of an individual difference in the P300 component, greater individual differences exist between users with respect to the aforementioned positive component at a latency from 700 ms to 900 ms, which is later in latency than P300. Therefore, the aforementioned positive component is preferably treated as having a broader breadth, e.g., a breadth of about 100 ms.

Thus, through the behavioral experiment and the electroencephalogram measurement experiment, the inventors have found that: (1) a speech sound intelligibility assessment is possible based on a user's confidence of aural distinction concerning an audio; and (2) a positive component of an event-related potential at a latency from 700 ms to 900 ms based on the point of audio presentation as a starting point reflects the confidence of aural distinction. Together, these have led to the finding that the positive component of the event-related potential can be used, by way of confidence of aural distinction with respect to an audio, as an index with which to evaluate difficulty of hearing. FIG. 10 shows correspondence between presence or absence of a positive component and confidence of aural distinction and ease of hearing, as compiled by the inventors. This correspondence diagram is created by taking the positive component at the electrode position Pz as an example.

Hereinafter, an adjustment device for a hearing aid according to an embodiment of the present invention will be described. The adjustment device for a hearing aid measures an electroencephalogram which is induced by a conversational voice that is input from an acoustic transducer section while the hearing aid is being used in daily life. Based on the presence or absence of a positive component in the event-related potential at a latency from 700 ms to 900 ms from each phoneme in the conversational voice as a starting point, the adjustment device evaluates the ease of hearing for each phoneme. When there is any phoneme that is difficult to hear, the adjustment device readjusts the hearing aid.

Embodiment 1

Hereinafter, with reference to the drawings, an embodiment of the adjustment device for a hearing aid will be described.

Figure 11:
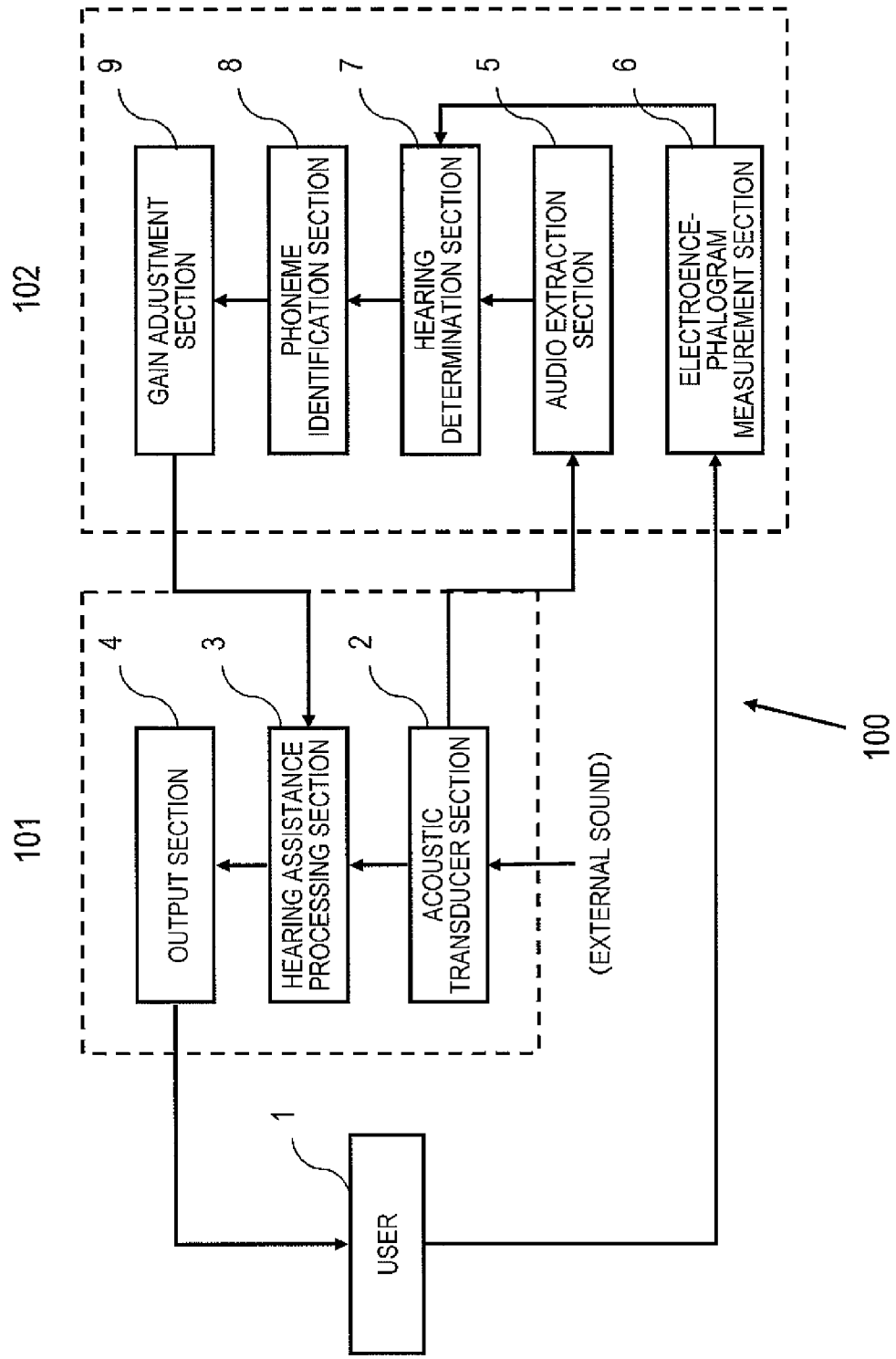
FIG. 11 is a diagram showing a construction and an environment of use for a hearing aid adjustment system 100.

FIG. 11 shows a construction and an environment of use for a hearing aid adjustment system 100. The hearing aid adjustment system 100 includes two portions: a hearing aid section 101 and a hearing assistance adjustment section 102. The hearing aid section 101 is a portion serving as a hearing aid, and includes an acoustic transducer section 2, a hearing assistance processing section 3, and an output section 4. In the hearing aid section 101, the acoustic transducer section 2 collects external sounds; the hearing assistance processing section 3 performs a hearing assistance process in accordance with the state of hearing of the user 1; and the output section 4 outputs the result to the user.

Figure 12:
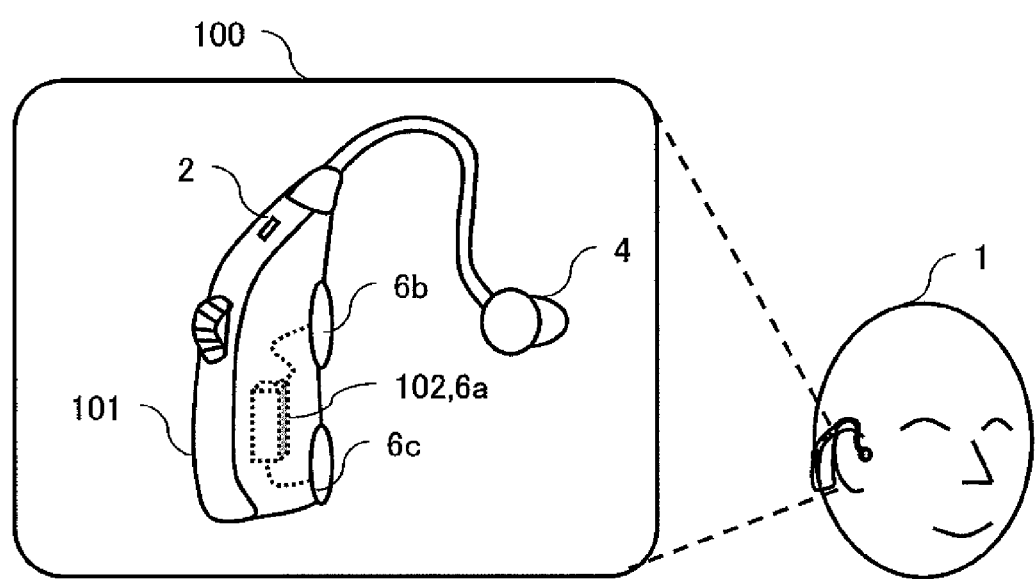
FIG. 12 is a diagram showing how the adjustment system 100 may be used.

FIG. 12 shows an exemplary scene where the adjustment system 100 may be used. A user is wearing on his or her ear a hearing aid adjustment system 100, in which a hearing aid 101 and an adjustment device 102 are integrated. The same reference numeral is assigned to any constituent element in FIG. 12 that corresponds to a constituent element in FIG. 11. For example, the acoustic transducer section 2 in FIG. 11 corresponds to a microphone 2 which is attached to the hearing aid. The output section 4 in FIG. 11 corresponds to a loudspeaker (receiver) for presenting a sound to the user. The hearing assistance processing section 3 in FIG. 11 corresponds to a signal processing circuit (chip circuit; not shown) which is internal to the hearing aid.

The hearing assistance adjustment section 102 in FIG. 11 performs additional processing outside the hearing aid section 101. The hearing assistance adjustment section 102 includes an electroencephalogram measurement section 6, an audio extraction section 5, a hearing determination section 7, a phoneme identification section 8, and a gain adjustment section 9. The electroencephalogram measurement section 6 measures an electroencephalogram of the user 1. The audio extraction section 5 extracts an audio portion from the sound information which is collected by the acoustic transducer section 2. Through mapping between the electroencephalogram measured by the electroencephalogram measurement section 6 and the sound information identified by the audio extraction section 5, an encephalic response with respect to each piece of sound information is measured. From that encephalic response, the hearing determination section 7 determines an evaluation of hearing by using a characteristic feature of the electroencephalogram pertaining to ease of hearing (of whose experiment and data have been described above). Thereafter, with respect to the result of hearing evaluation, if a shift in the latency of the electroencephalogram has induced a determination that a plurality of characters (i.e., the phonemes or syllables represented thereby) are difficult to hear, the phoneme identification section 8 performs a process for eliminating such ambiguity, and the gain adjustment section 9 performs an adjustment for addressing the respective difficulty of hearing. This adjustment is performed for the hearing assistance processing section 3, and is to be reflected on the subsequent hearing assistance process by the hearing aid section 101.

The hearing assistance adjustment section 102 in FIG. 11 corresponds to a circuit 102 and the like shown in FIG. 12. More specifically, the electroencephalogram measurement section 6 in the hearing assistance adjustment section 102 of FIG. 11 includes an electroencephalograph main body 6a, which is a circuit for amplifying a biological signal, and electrodes 6b and 6c. An electroencephalogram is measurable by measuring a potential difference between at least two electrodes which are mounted on the head and its neighborhood. In the illustrated example, electrodes 6b and 6c are placed in portions at which the hearing aid main body 101 will come into contact with an ear of the user. Nowadays, hearing aids may be simultaneously worn on both ears for improved performance and comfort, in which case the electroencephalogram measurement can be made based on a potential between both ears, thus facilitating the monitoring of the encephalic activity.

In the above-described electroencephalogram measurement experiment, the electrodes are placed on the scalp. However, it should also be possible to place the electrodes at other positions. As shown in FIG. 9, the C3-Cz-C4 potential distribution pattern is inverted both in the case of a high confidence of aural distinction and the case of a low confidence of aural distinction, which makes it presumable that confidence of aural distinction can be determined also by placing the electrodes at further outside of the electrode positions C3 and C4, e.g., around an ear position.

Figure 13:
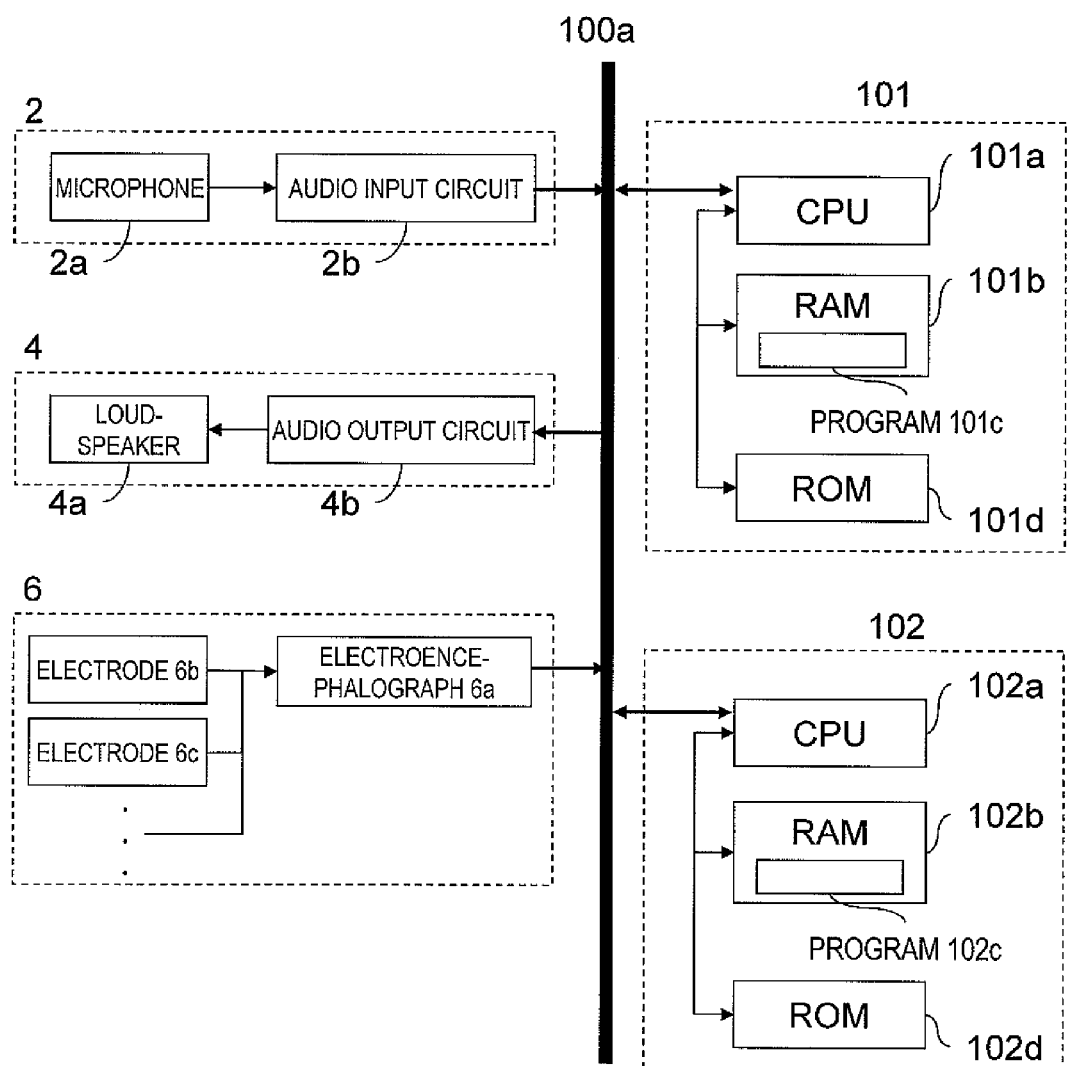
FIG. 13 is a diagram showing the hardware construction of the hearing aid adjustment system 100 according to the present embodiment.

The other constituent elements of the hearing assistance adjustment section 102 are mainly functional portions that perform signal processing. These are implemented as internalized parts in the hearing aid main body, as shown in FIG. 13. As such parts, DSPs, memories, and the like are contemplated, for example. Hereinafter, these will be more specifically described.

FIG. 13 shows a hardware construction of the hearing aid adjustment system 100 according to the present embodiment. As the hardware of the hearing aid adjustment system 100, a CPU 101a, a RAM 101b, and a ROM 101d are provided for handling the signal processing in the hearing aid section 101. A program 101c of the processing is stored in the RAM 101b. Similarly, a CPU 102a, a RAM 102b, and a ROM 102d are provided for handling the signal processing in the hearing assistance adjustment section 102. A program 102c of the processing is stored in the RAM 102b.

As devices handling the input/output to/from the exterior, a microphone 2a and an audio input circuit 2b are provided as the acoustic transducer section 2, and a loudspeaker (receiver) 4a and an audio output circuit 4b are provided are provided as the output section 4. In the electroencephalogram measurement section 6, an electroencephalograph 6a, an electrode 6b, and an electrode 6c are provided.

These devices are interconnected via a bus 100a so that data exchange among them is possible. For example, a signal of the audio that has been collected by the acoustic transducer section 2 is subjected to a hearing assistance process by the CPU 101a in accordance with the program 101c stored in the RAM 101b, and is sent to the output section 4.

Note that the hearing aid adjustment system 100 may be constructed from one set of a CPU, a RAM, and a ROM, or implemented as a piece of hardware (e.g., DSP) consisting of a semiconductor circuit having computer programs incorporated therein. Such a DSP can realize all functions of the aforementioned CPUs, RAMs, ROMs, audio input/output circuits, and the like on a single integrated circuit.

The aforementioned computer programs 101c and 102c may be distributed on the market in the form of a product recorded on a storage medium such as a CD-ROM, or transmitted through telecommunication lines such as the Internet.

Next, the processing performed in the hearing aid adjustment system 100 as such will be described in detail with reference to FIGS. 14 to 22.

FIG. 14A shows a procedure of processing which is performed by a usual hearing aid, whereas FIG. 14B shows in outline a combined procedure including the processing performed by the hearing aid adjustment system 100 of the present embodiment. Those steps which need more explanation than just an outline will be described later based on more detailed flowcharts.

FIG. 14A shows an outline of the flow of processes in the hearing aid.

At step S20, the acoustic transducer section 2 collects external sounds.

At step S30, the hearing assistance processing section 3 performs a hearing assistance process. The hearing assistance process is a process of resolving an audio collected at step S20 into powers at respective frequencies, and restoring the audio after performing a predetermined amplification for each frequency. In the present specification, the predetermined amplification performed for each frequency is referred to as a "hearing assistance process", and changing a predetermined value representing the gain defining an adjustment for each frequency is referred to as a "gain adjustment".

At step S40, the output section 4 outputs a result of the hearing assistance process to the user. Specifically, the output section 4 outputs an adjusted audio, which will be easier for the user 1 to hear than that before the adjustment.

FIG. 14B shows an outline of the entire flow of processes in the adjustment system, which is inclusive of the aforementioned processes. In this figure, any step where the same process that is performed by the hearing aid is denoted by the same numeral as that in FIG. 14A, and the description thereof is omitted. What is additional to the aforementioned hearing aid process is steps S50 to S90 (which are sandwiched between process steps S20 and S30 of the hearing aid), where a hearing assistance adjustment process is performed.

At step S50, the audio extraction section 5 cuts out an audio signal. In the aforementioned electroencephalographic experiment by the inventors, the audio was presented on a sound-by-sound basis. On the other hand, it is a continuous audio that a user will actually hear in daily scenes, which makes it necessary to cut out an audio signal.

At step S60, the electroencephalogram measurement section 6 measures an electroencephalogram. Since electroencephalographs are decreasing in size and power consumption in the recent years, it is possible to realize a device in which an electroencephalograph is combined with a hearing aid. In the case where the hearing aid adjustment system 100 is of a type which is worn by using one ear, a plurality of electrodes of a downsized electroencephalograph may be placed at positions where the hearing aid comes into contact with the skin of the head. In the case where the hearing aid adjustment system 100 is of a type which is worn by using both ears, the electrodes can be placed respectively at both ears. In the latter case, an electroencephalogram between both ears also becomes available. In the case of a headphone-type shape, an electroencephalogram on the head will also be measurable.

Measured electroencephalogram presumably contains various information. However, through association with stimulations, e.g., an event-related potential, the tendency of an evoked potential responsive to an audio presentation can be grasped.

At step S70, the hearing determination section 7 extracts electroencephalogram signals associated with the audio signal which has been cut out by the audio extraction section 5. By extracting each electroencephalogram component, the hearing determination section 7 determines a state of hearing.

At step S80, if it so appears that there is a plurality of prospective sounds that were difficult to hear, the phoneme identification section 8 identifies one that was actually difficult to hear from among the results output from the hearing determination section 7.

At step S90, the gain adjustment section 9 adjusts a gain for a phoneme or syllable that was difficult to hear. Generally speaking, each individual adjustment method for hearing aids may be effective for specific phonemes but other phonemes may be unfavorably affected by it, etc., thus having difficulties in providing adjustments for any and all sounds. What is effective is, then, to perform an adjustment for phonemes that are difficult to hear.

In the above-described flow, the process of cutting out an audio signal (step S50), the hearing determination process (step S70), the phoneme identification process (step S80), and the gain adjustment process (step S90), which are of particular relevance to the present invention, will be described in detail with further reference to respective flowcharts and figures.

Figure 15:
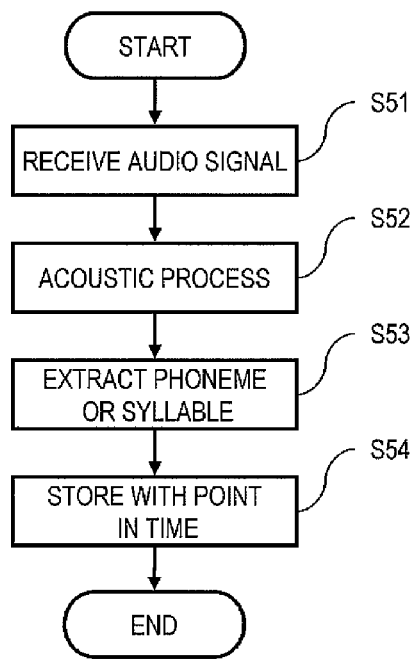
FIG. 15 is a diagram showing the detailed processing by an audio extraction section 5.
Figure 16:
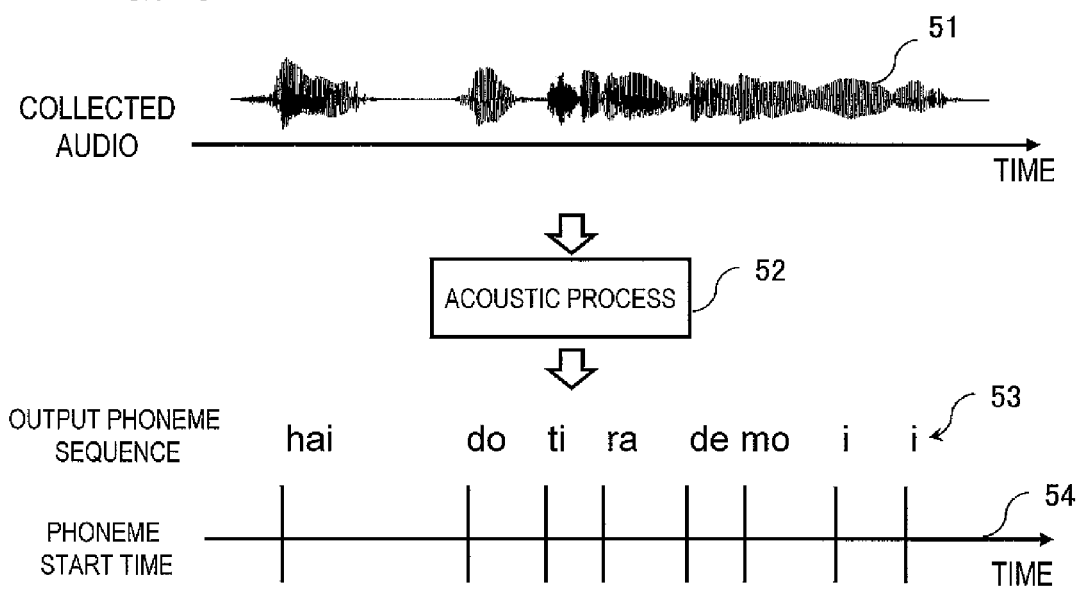
FIG. 16 is a specific explanatory diagram of the processing by the audio extraction section 5.

FIG. 15 shows details of the flow of processes by the audio extraction section 5, and FIG. 16 is an explanatory diagram illustrating these processes. Hereinafter, descriptions will be given on the basis of the flowchart of FIG. 15, and optionally in association with FIG. 16.

At step S51, the audio extraction section 5 acquires the audio signal which has been collected by the acoustic transducer section 2. Specifically, the collected audio is taken into the audio extraction section 5 every certain period (timing), so as to each span a certain duration. In the example shown in FIG. 16, the audio extraction section 5 takes in a collected audio signal 51 which is represented as "collected audio".

At step S52, the audio extraction section 5 converts the collected audio signal 51 into a phoneme sequence at the acoustic process 52 (FIG. 16). The phoneme sequence after conversion is subjected to an extraction process of step S53.

The acoustic process at step S52 is a process of detecting what kinds of phonemes or syllables are contained in the audio data, and is one that is used for preliminary processes in the field of speech recognition. Specifically, the acoustic process in the present embodiment is a process of subjecting the current data to comparison calculations against stored acoustic data of phonemes and syllables (e.g., standard audio waveforms and characteristic amounts therefor), in order to phonetically recognize the current speech.

At step S53, based on the result of the acoustic process of step S52, the audio extraction section 5 extracts and outputs a sequence of phonemes or syllables. FIG. 16 illustrates an example where, as a result of the acoustic process 52, a phoneme sequence 53 [hai/do/ti/ra/de/mo/i/i] has been extracted. In the present specification, the extracted phonemes are partitioned at the syllable level. However, the resolution of extraction may be changed as appropriate. For example, a phoneme level partitioning may be employed, e.g., [h/a/i/d/o/u/m/o]. Similar processing to the above would also be possible through partitioning in greater units, e.g., at the word level or per silent period. Recognition of words may be achieved by, for example, the audio extraction section 5 storing dictionary data in which phoneme sequences are associated with words, and checking the dictionary data for the phoneme sequence 53.

At step S54, the audio extraction section 5 establishes mapping as to which point in time each syllable extracted as the output phoneme sequence 53 was uttered, and stores such pairs.

This process ultimately provides information as to the currently-uttered syllable and the corresponding point in time at which that syllable was uttered. Based on this correspondence, the knowledge of the electroencephalographic experiment (event-related potential measuring experiment) described at the beginning of the present specification can be put to use. Specifically, by cutting out an electroencephalogram for each syllable and determining an electroencephalographic feature for each individual syllable, an evaluation of hearing can be determined.

Figure 17:
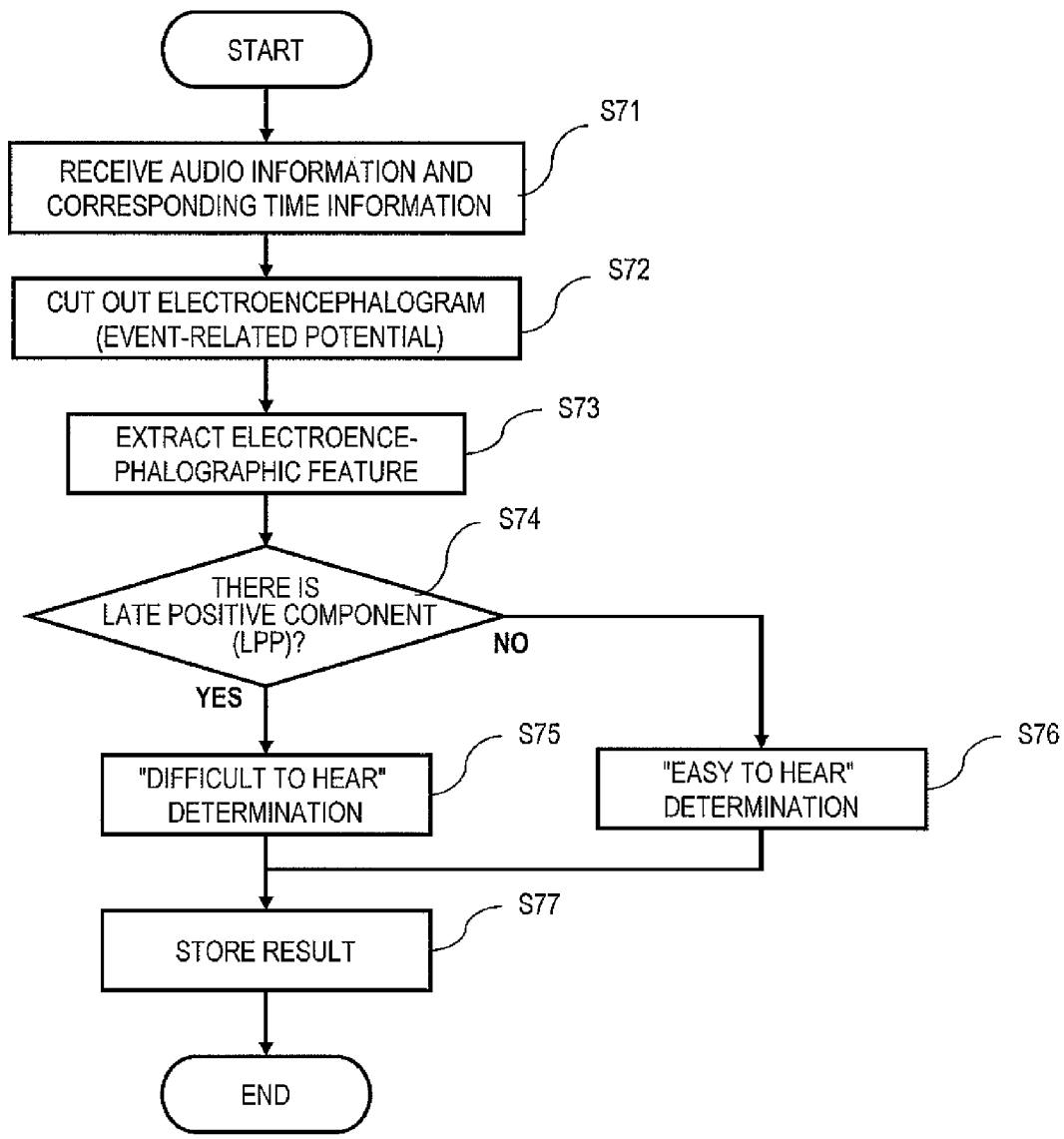
FIG. 17 is a flowchart showing a procedure of processing by a hearing determination section 7.

Next, the hearing determination process shown at step S70 in FIG. 14B will be described in detail. The hearing determination process is performed by the hearing determination section 7 (FIG. 11). FIG. 17 shows a procedure of processing performed by the hearing determination section 7. FIG. 18 shows an exemplary data processing in the hearing determination process.

At step S71 in FIG. 17, the hearing determination section 7 receives syllable information and corresponding time information 71 (FIG. 18) from the audio extraction section 5. From the time information 71, the point of utterance of each phoneme can be identified.

At step S72, after receiving electroencephalogram data from the electroencephalogram measurement section 6, the hearing determination section 7 extracts event-related potentials, each based on a point in time which is contained in the time information 71 corresponding to a syllable as a starting point. An event-related potential is a piece of electroencephalographic information that is measurable in connection with a given event (which in this case is the utterance of a syllable). An event-related potential is obtained by cutting out a predetermined zone (e.g., a zone 72a from −100 ms to 1000 ms), based on the point of time at which the syllable was uttered, from the electroencephalogram. Such a zone of the electroencephalogram is to be cut out with respect to each syllable. FIG. 18 shows event-related potentials 72b that have been cut out.

At step S73, the hearing determination section 7 extracts an electroencephalographic feature for analysis from each event-related potential 72b having been cut out. The electroencephalographic feature of interest here is a characteristic positive component at e.g. 800 ms±100 ms. As the characteristic amount for analysis, the maximum amplitude or zone average potential for a latency from 700 ms to 900 ms, or Wavelet coefficients or the like can be used, for example.

At step S74, with respect to each electroencephalographic feature obtained at step S73, the hearing determination section 7 determines whether any component related to difficulty of hearing (e.g., a late positive component (LPP) in the case where an electroencephalogram is measured at Pz) is contained. If it is determined that an LPP is contained, control proceeds to step S75; if not, control proceeds to step S76.

As an example of this determination method, the maximum amplitude or zone average potential may be compared against a predetermined threshold to determine whether an LPP is contained or not. Alternatively, a similarity level (e.g., a correlation coefficient) may be determined between the electroencephalographic feature and a predetermined template of an electroencephalogram waveform which is generated from the waveform of a typical positive component signal at a latency from 700 ms to 900 ms. FIG. 18 schematically illustrates comparing an event-related potential 72b having been cut out against a waveform 73 of an LPP when there is difficulty of hearing. Through the comparison, any case of similarity may be determined as "there is a positive component", and any case of non-similarity may be determined as "there is no positive component". The predetermined threshold value or template may be calculated or generated from a prestored waveform of a positive component of a generic user, or calculated or generated from the waveform of a positive component of each individual person.

At step S75, the hearing determination section 7 makes a "difficult to hear" determination.

At step S76, the hearing determination section 7 makes an "easy to hear" determination.

At step S77, the hearing determination section 7 stores the results of hearing determination. The results of hearing determination are stored into a table, e.g., as results of determination 77 (FIG. 18). The respective columns of the table represent syllables, with a result of determination being stored for each syllable. As described in FIG. 18, for example, an "easy to hear" result is stored for "hai" and "ra", whereas a "difficult to hear" result is stored for "do" and "ti".

The hearing determination process performed through such processing allows an evaluation of hearing to be made for each syllable even during a usual continuous speech.

However, there remains a question as to which character (or, the phoneme or syllable represented thereby) was difficult to hear. This issue presumably arises because the characteristic zone in the electroencephalogram spans a broader breadth than the transition between syllables (speed of speech).

This will be specifically described below. A standard speed of utterance is approximately 8 to 12 morae (=syllables). For example, in the Japanese language, a speech speed of 10 morae/second is a standard possibility. Therefore, it is expected that there exists about 100 ms after a certain syllable is uttered and until a next syllable is uttered.

On the other hand, according to the electroencephalogram measurement experiment conducted by the inventors, the characteristic feature of the electroencephalogram that is related to difficulty of hearing appears between 700 ms and 900 ms, which is a fairly late latency zone in the field of event-related potential studies. Usually, the error in the latency of an event-related potential increases toward later latency zones. In the illustrated example of the present embodiment, the error in the latency of the relevant event-related potential is expected to be about ±100 ms. In fact, also in the electroencephalographic experiment conducted by the inventors, the zone in which any significant difference was recognized spanned a broad breadth of 730 ms to 915 ms (FIG. 8).

By taking both of the above characteristics into consideration, when a single subjective phenomenon that feels "difficult to hear" has occurred, a number (e.g., 2, 3, or 4) of successive phonemes or syllables are likely to receive a determination that the electroencephalogram contains the characteristic component, from the perspective of errors in electroencephalogram latency. In this case, as in the results of hearing determination 77, for example, a number of successive syllables (do, ti) will receive a "difficult to hear" processing result. However, a more effective hearing aid adjustment will be enabled if the syllable that is the actual cause can be determined. If a number of phonemes or syllables are detected that are determined as difficult to hear, the chronologically preceding sound (the sound that appeared first) may well be treated as the sound that was difficult to hear, so as to be subjected to the adjustment process described later.

Generally speaking, in the final adjustment of a hearing aid, each individual adjustment method may be effective for specific phonemes but unfavorably affect other phonemes because the frequency characteristics pattern differs for each phoneme. This leads to the characteristics that an adjustment which can address any and all sounds is difficult to make, and that a more accurate adjustment will be enabled if it is possible to narrow down to one phoneme that is difficult to hear.

Therefore, when a plurality of prospective syllables that may be difficult to hear are found through the hearing determination process, it is necessary to identify which syllable was the most difficult to hear. In the present embodiment, this is done by the phoneme identification section 8. A process of the phoneme identification section 8 utilizing the auditory characteristics that the inventors take note of will be described.

Now, the phoneme identification process shown in step S80 of FIG. 14B will be described in detail. The phoneme identification process is performed by the phoneme identification section 8 (FIG. 11).

Figure 19:
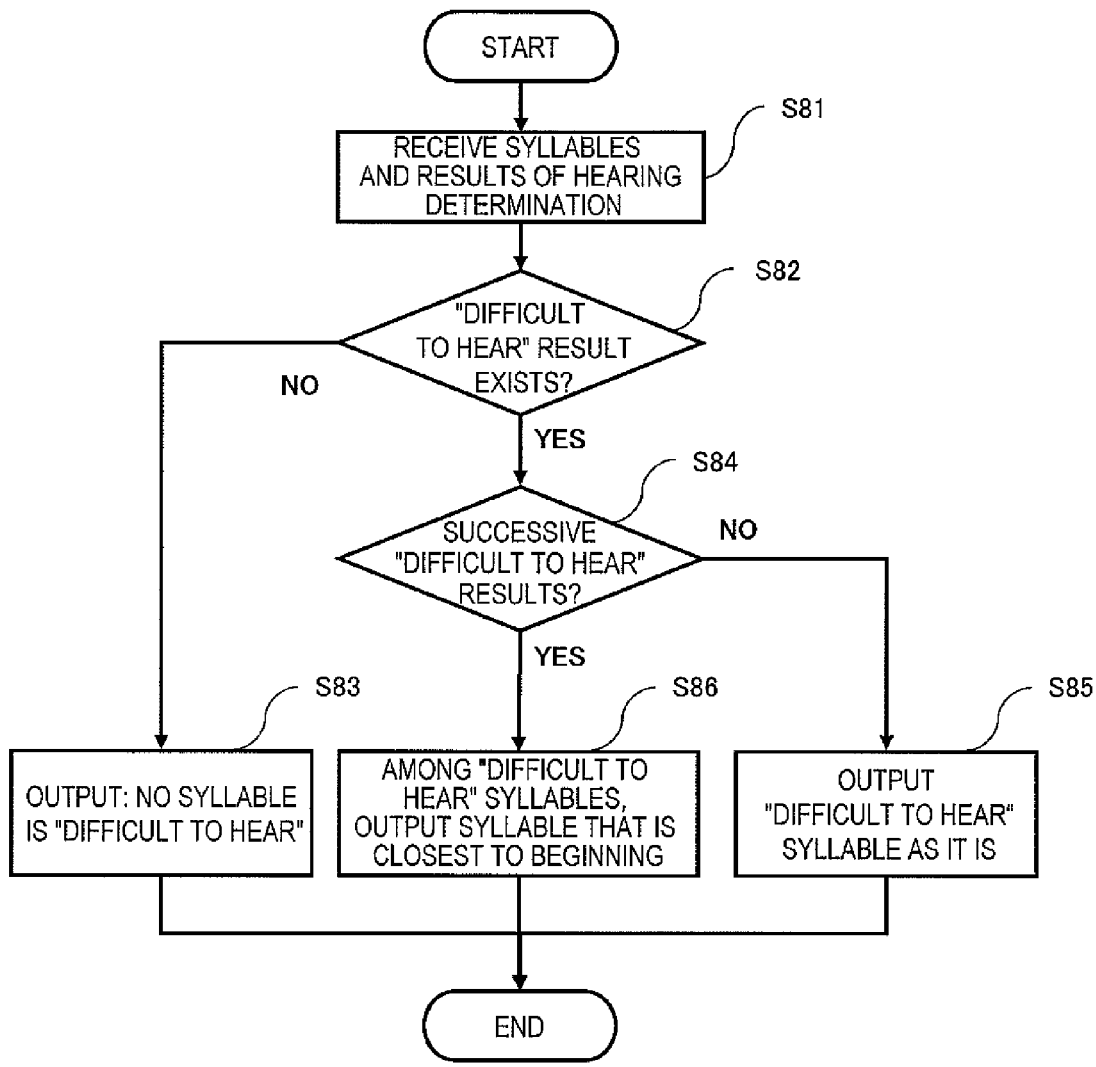
FIG. 19 is a flowchart showing a procedure of processing performed by a phoneme identification section 8.
Figures 20, 21:
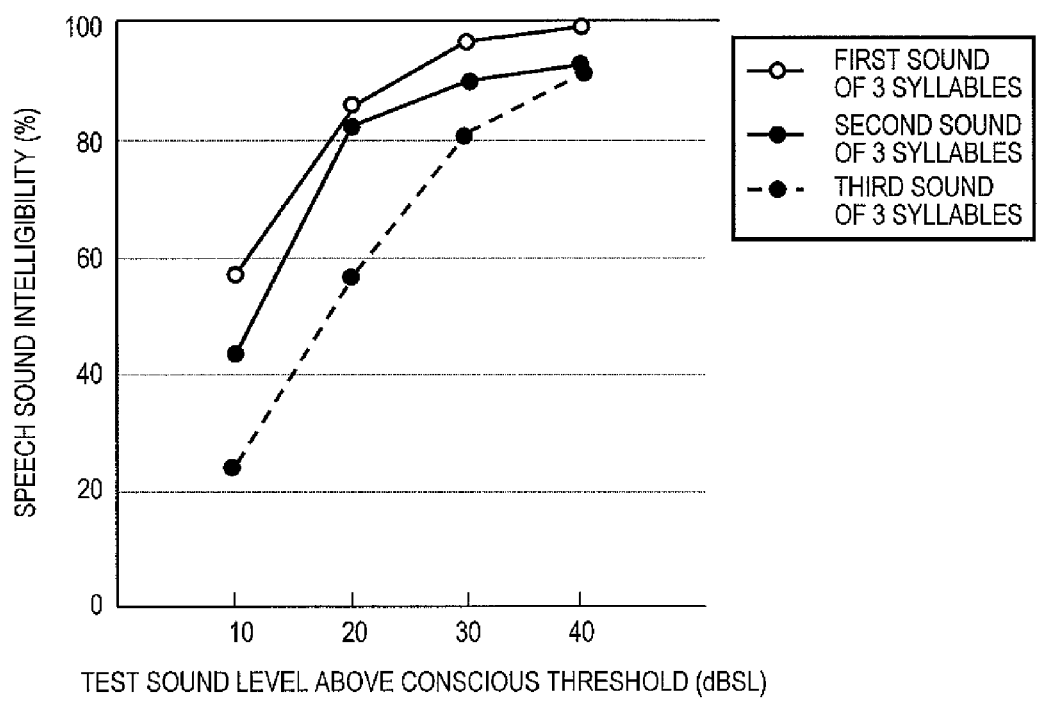
FIG. 20 is a diagram showing data of auditory characteristics serving as a principle of a phoneme identification process.
FIG. 21 is an illustrative example showing how the adjustment method to be performed may differ depending on the type of consonant contained in a syllable considered as difficult to hear.

FIG. 19 shows a procedure of processing performed by the phoneme identification section 8. FIG. 20 shows data of auditory characteristics serving as a principle of a phoneme identification process. Hereinafter, descriptions will be given on the basis of the flowchart of FIG. 19, and optionally in association with the auditory principle of FIG. 20.

At step S81, the phoneme identification section 8 receives syllables and results of hearing evaluation from the hearing determination section 7.

At step S82, the phoneme identification section 8 determines whether any "difficult to hear" result exists among the results of hearing evaluation or not. If no "difficult to hear" result exists, control proceeds to step S83 to make an output that there is no syllable that is "difficult to hear", and the process is ended. If any "difficult to hear" result exists, control proceeds to step S84.

At step S84, the phoneme identification section 8 makes a determination as to whether there are successive "difficult to hear" evaluation results. If "difficult to hear" evaluation results are not occurring successively, control proceeds to step S85 to output the one "difficult to hear" syllable as a result, and the process is ended. If "difficult to hear" evaluation results are occurring successively, control proceeds to step S86. When control proceeds to step S86, it is determined that there is some ambiguity as to syllable identification because of the electroencephalogram latency and the speed of speech.

At step S86, among the successive "difficult to hear" syllables, the phoneme identification section 8 selects the syllable that is the closest to the beginning as the syllable that was the most difficult to hear, outputs this as the result, and ends the process. For example, in the results of hearing determination 77 shown in FIG. 18, "do" and "ti" are the prospects. Between these, the phoneme identification section 8 determines "do" as the final result.

The reason why this process is effective will be described along with the auditory principle of FIG. 20.

FIG. 20 shows intelligibility curves for the first sound, second sound, and third sound of a 3-syllabled nonword. These intelligibility curves are cited from Kazuoki KODERA, "HOCHO NO SHINPO TO SHAKAITEKI OUYOU" (or "Advances In Hearing Assistance And Social Applicability"), Shindan To Chiryosha, 2006, p. 67. These intelligibility curves are evaluation results of speech sound intelligibility for eight people with normal hearing. The horizontal axis represents the test sound level above a hearing threshold level, indicating the loudness of a sound which the test subject hears (unit: dBSL), and the vertical axis represents speech sound intelligibility (unit: %). In the evaluation results presented, the test sound level is varied between four levels from 10 dB to 40 dB; and at each level, the intelligibilities of the first sound, the second sound, and the third sound are respectively plotted.

According to this graph, in a meaningless three-syllable non-word, the first sound has the lowest speech sound intelligibility, followed by the second sound and the third sound having increasingly better intelligibilities.

These results point to the finding that the first sound is possibly the most difficult syllable to hear in a nonword, too, where there is no context that is suggested by preceding or following syllables. An objective of the present invention is to identify syllables that are difficult to hear in the speech that may occur in dialogue scenes of daily life. Even concerning this objective, the inventors have realized that, when electroencephalogram processing produces a plurality of successive prospects that are determined as difficult to hear, it is effective to determine the syllable that is the closest to the beginning to be the most difficult to hear. The illustrated experimental conditions are directed to a nonword-based experiment; however, in daily conversations, a word is often estimated based on its context which is implied by preceding or following characters. However again, such context implied by preceding or following characters is of least use for the first sound, which makes it reasonable to select a syllable that is the closest to the beginning as the syllable that is the most difficult to hear.

A sound at the beginning may or may not be included among the prospects that are difficult to hear. Based on the findings from FIG. 20, however, sounds that are closer to the beginning tend to be more difficult to hear, which makes it reasonable to select a sound that is close to the beginning as a syllable that is difficult to hear.

The relationship between these experimental results and a continuous audio can be considered as follows. Even in dialogue sentences, audio data is likely to contain many silent periods, however short they may be. If a piece of speech is to be divided at such silent periods, even a continuous audio can be regarded as repetitions of sporadic utterances that each span a plurality of words. Since electroencephalogram latency also fluctuates by about ±100 ms, the hypothesis should hold true that what lies between a silent period and another silent period may safely be regarded as a succession of words etc., because silent periods on the order of several hundred milliseconds will also be found in any continuous audio.

Lastly, as the last step in the readjustment of a hearing aid, the gain adjustment process will be described. The gain adjustment process is performed by the gain adjustment section 9 (FIG. 11). Specifically, if there exists any "difficult to hear" syllable that has been identified by the phoneme identification section 8, then the phoneme identification section 8 adopts certain hearing assistance processes or the like by referring to a table shown in e.g. FIG. 21, thus to improve only the sound(s) that is difficult to hear.

The table of FIG. 21 illustrates an example as to how the adjustment method to be performed may differ depending on the type of consonant contained in a syllable that is determined as difficult to hear. The gain adjustment section 9 retains this table in an internal memory or buffer (not shown), and on the basis of this table, conducts either an expansion of consonant portions or an expansion-compression of consonant portions. This table is previously generated based on accumulated research on hearing aids concerning consonants that are difficult to hear and readjustment processes corresponding thereto (e.g., Kazuoki KODERA, "HOCHO NO SHINPO TO SHAKAITEKI OUYOU" (or "Advances In Hearing Assistance And Social Applicability"), Shindan To Chiryosha, 2006, p. 78).

For example, expansion of consonant portions is effective for the unvoiced consonant h, the voiced consonants d and g, and the like. On the other hand, expansion-compression of consonant portions is effective for the unvoiced consonant ts and the like. By performing a readjustment based on the rules shown in this table, adjustment is performed with respect to only the consonants that are difficult to hear.

As described above, according to the present invention, moments at which a user feels difficulties of hearing and the relevant syllables are identified through an electroencephalogram analysis, and readjustments which are suitable for the identified syllables can be performed. As a result, the user is free of the trouble of having to memorize situations where difficulties of hearing were felt and visit a hearing aid shop to offer explanations to an expert for readjustment. Instead, readjustments are possible in situ, i.e., at the place where any difficulty of hearing is felt, whereby the user's burden can be reduced.

In the description of the above Embodiments, it is assumed that the electrode position(s) is at Pz, etc., according to the International 10-20 system, for example. However, it is difficult to identify an exact electrode position on each user that corresponds to the Pz position. Therefore, the electrode position may be a position that is fairly deemed as Pz (position in the neighborhood of Pz). The event-related potential will be correctly measured at any position in the neighborhood of Pz. The same is also true of Cz and other electrode positions.

(Variant)

Hereinafter, variants of the hearing aid adjustment system 100 according to the above-described embodiment will be described.

First, the adjustment device for a hearing aid 100 may be provided in a form which lacks the hearing aid function. Specifically, only the hearing assistance adjustment section 102 in FIG. 11 may be provided. In this case, the hearing aid section 101 is a usual hearing aid. However, the hearing aid section 101 should have an interface for receiving gain adjustments from an external PC or the like. Via this interface, the audio extraction section 5 of the hearing assistance adjustment section 102 receives audio information (audio signal) from the acoustic transducer section 2 of the hearing aid section 101. Then, an instruction for gain adjustment is given from the hearing assistance adjustment section 102 to the hearing assistance processing section 3 of the hearing aid section 101. Note that the hearing aid section 101 may be of a type which does not output audio information to the hearing assistance adjustment section 102 but which only receives gain adjustments therefrom, in which case the hearing assistance adjustment section 102 should have a function similar to the acoustic transducer section.

Moreover, the gain adjustment section 9 may be omitted from the hearing assistance adjustment section 102, so that the hearing assistance adjustment section 102 is only used for making evaluations. In this case, the hearing assistance adjustment section 102 may output evaluation results to an externally-provided gain adjustor (not shown) which has a similar function to that of the gain adjustment section 9.

Furthermore, the electroencephalogram measurement section 6 may be omitted from the hearing assistance adjustment section 102. The electroencephalogram measurement section 6 may be provided external to the hearing assistance adjustment section 102, and connected to the hearing assistance adjustment section 102.

Figure 22:
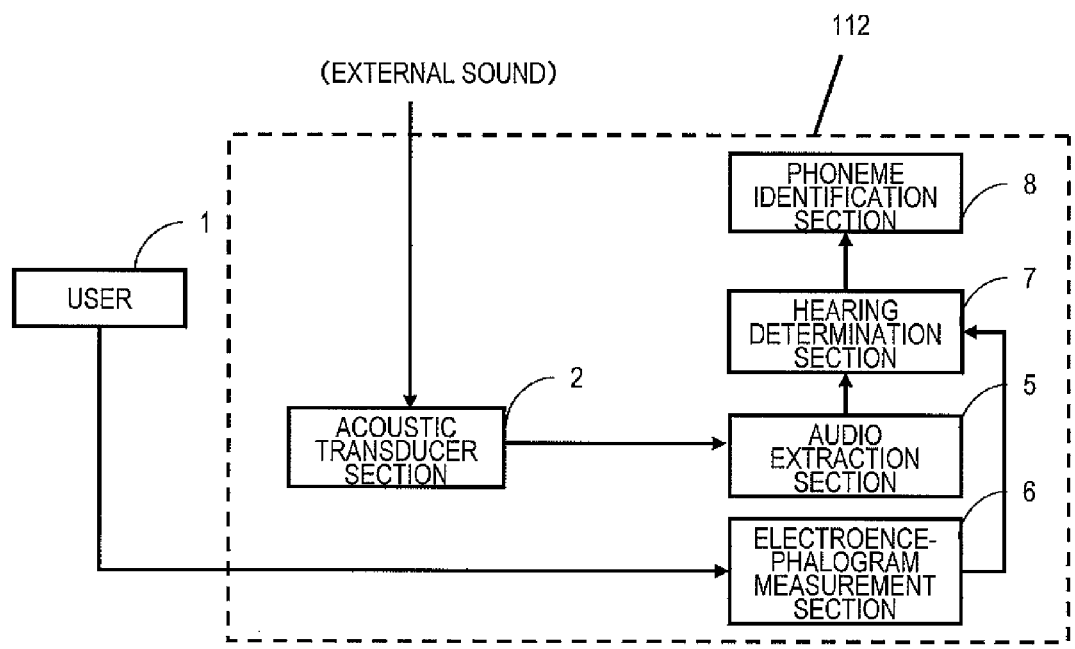
FIG. 22 is a diagram showing the construction of a hearing assistance evaluation apparatus 112.

FIG. 22 shows the construction of a hearing assistance evaluation apparatus 112 according to a variant. The difference between the hearing assistance evaluation apparatus 112 and the hearing assistance adjustment section 102 (FIG. 11) is that the gain adjustment section 9 of FIG. 11 is not provided in the hearing assistance evaluation apparatus 112 and that an acoustic transducer section 2 is provided. Otherwise, the construction is the same, and the descriptions of the respective constituent elements are therefore omitted.

This construction makes it possible to collect evaluation data. As compared to the example shown in FIG. 12, the output section 4 is not essential to the hearing assistance evaluation apparatus 112, and the hearing assistance evaluation apparatus 112 does not need to be downsized, unlike the hearing assistance adjustment section 102.

Moreover, the acoustic transducer section 2 and/or the electroencephalogram measurement section 6 may be omitted from the construction of the hearing assistance evaluation apparatus 112 shown in FIG. 22. By externally providing the acoustic transducer section 2 and/or the electroencephalogram measurement section 6 and allowing them to be connected to the hearing assistance evaluation apparatus 112, the same operation as that of the hearing assistance evaluation apparatus 112 shown in FIG. 22 can be realized. For example, the hearing assistance evaluation apparatus 112 can be composed of a high-performance microphone, a larger-sized electroencephalograph for medical/research purposes, and a PC. There is no need to develop downsizing techniques, and existing microphones, electroencephalographs, PC, and computer programs will become available for the implementation, thus allowing for cost reduction.

A possible situation in which such may be used is where a fitter who is responsible for adjustments of a hearing aid in a hearing aid shop places the hearing assistance evaluation apparatus 112 on the user, and evaluates his or her hearing from an electroencephalogram while a dialogue is being held between them, for example. With the function of the phoneme identification section 8, information of evaluation results as to where in the dialogue the user has felt difficulties of hearing can be accumulated in an internal memory (not shown). Alternatively, the recorded information may be output to a monitor (not shown), and to a separately provided gain adjustor for adjusting the gain. Note that the hearing assistance evaluation apparatus 112 may output the evaluation result information in real time. Based on this information, the fitter can make an appropriate gain adjustment. Even though no automatic gain adjustment method has been established yet that takes care of all aspects of hearing (e.g., pure tones as well as conversational sounds), the present method makes it possible to adjust the hearing assistance process in accordance with the difficulties of hearing which are actually being felt by the user.

Other than making adjustments in a hearing aid shop, the hearing assistance evaluation apparatus 112 may also be used in any workplaces, public places, or homes where users may lead their usual lives. For example, before purchasing a hearing aid, the hearing assistance evaluation apparatus 112 may be leased to a user from a hearing aid shop. Then, as the user leads his or her usual daily life, the hearing assistance evaluation apparatus 112 takes electroencephalogram measurements, thus recording and accumulating information as to which dialogue in which situation the user has felt difficulties of hearing. Referring to this accumulated data, a fitter at the hearing aid shop can recommend a hearing aid of an optimum form, and/or a gain adjustment therefor.

An adjustment device for a hearing aid according to the present invention utilizes an electroencephalogram to detect difficulties of hearing that a user of a hearing aid is expected to encounter daily, and enables in-situ readjustments. Therefore, it can be used in a wide variety of scenes where the hearing aid may be used.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An adjustment device for a hearing aid, comprising:
   an acoustic transducer section for collecting ambient sounds and outputting an audio signal;
   an audio extraction section for utilizing information of a phoneme or syllable contained in the audio signal to output time information, the time information identifying a point in time of uttering the phoneme or syllable;
   an electroencephalogram measurement section for measuring an electroencephalogram signal of a user;
   a hearing determination section for determining a difficulty of hearing of the phoneme or syllable by relying on an event-related potential based on the identified point of uttering the phoneme or syllable as a starting point, the event-related potential being acquired from the electroencephalogram signal measured by the electroencephalogram measurement section;
   a phoneme identification section for, when a plurality of phonemes or syllables are determined by the hearing determination section as difficult to hear, identifying a phoneme or syllable closest to a beginning among the plurality of phonemes or syllables to be difficult to hear; and
   a gain adjustment section for, with respect to the phoneme or syllable identified by the phoneme identification section, determining a gain adjustment method based on a type of the phoneme or syllable, and adjusting a gain of the outputted audio signal for the phoneme or syllable based on the determined gain adjustment method.

2. The adjustment device of claim 1, wherein the hearing determination section determines the difficulty of hearing of the phoneme or syllable based on whether a predetermined characteristic component is contained in an event-related potential at 800 ms±100 ms since the point of uttering the phoneme or syllable as a starting point.

3. The adjustment device of claim 2, wherein the electroencephalogram measurement section measures the electroencephalogram signal by utilizing an electrode adapted to be placed in a neighborhood of Pz of the user according to the International 10-20 system.

4. The adjustment device of claim 3, wherein the hearing determination section determines that the phoneme or syllable is difficult to hear when a positive component is contained in the event-related potential.

5. The adjustment device of claim 2, wherein the electroencephalogram measurement section measures the electroencephalogram signal by using an electrode adapted to be placed in a neighborhood of Cz of the user according to the International 10-20 system.

6. The adjustment device of claim 5, wherein the hearing determination section determines that the phoneme or syllable is difficult to hear when a negative component is contained in the event-related potential.

7. An adjustment device for a hearing aid, comprising:
   an audio extraction section for outputting time information by utilizing information of a phoneme or syllable contained in an audio signal of an ambient sound collected by an acoustic transducer section for collecting ambient sounds, the time information identifying a point in time of uttering the phoneme or syllable;
   a hearing determination section for determining a difficulty of hearing of the phoneme or syllable by relying on an event-related potential based on the identified point of uttering the phoneme or syllable as a starting point, the event-related potential being acquired from an electroencephalogram signal of a user measured by an electroencephalogram measurement section for measuring the electroencephalogram signal; and
   a phoneme identification section for, when a plurality of phonemes or syllables are determined by the hearing determination section as difficult to hear, identifying a phoneme or syllable closest to a beginning among the plurality of phonemes or syllables to be difficult to hear, wherein
   the adjustment device outputs information of the phoneme identified by the phoneme identification section
   a gain adjustment section for, with respect to the phoneme or syllable identified by the phoneme identification section, determining a gain adjustment method based on a type of the phoneme or syllable, and adjusting a gain of the outputted audio signal for the phoneme or syllable based on the determined gain adjustment method.

8. The adjustment device of claim 7, wherein the adjustment device outputs the information of the phoneme identified by the phoneme identification section to a gain adjustment section for adjusting a gain for outputting an audio signal for the phoneme.

9. An adjustment method for a hearing aid, comprising the steps of:

collecting ambient sounds and outputting an audio signal;

utilizing information of a phoneme or syllable contained in the audio signal to output time information, the time information identifying a point in time of uttering the phoneme or syllable;

measuring an electroencephalogram signal of a user;

determining a difficulty of hearing of the phoneme or syllable by relying on an event-related potential based on the identified point of uttering the phoneme or syllable as a starting point, the event-related potential being acquired from the measured electroencephalogram signal;

when a plurality of phonemes or syllables are determined as difficult to hear in the determination step, identifying a phoneme or syllable closest to a beginning among the plurality of phonemes or syllables to be difficult to hear; and with respect to the identified phoneme or syllable, determining a gain adjustment method based on a type of the phoneme or syllable, and adjusting a gain for outputting an audio signal for the phoneme or syllable based on the determined gain adjustment method.

10. A non-transitory computer-readable medium storing a computer program to be executed by a computer for adjustment of a hearing aid, wherein the computer program causes the computer to execute the steps of: receiving an audio signal of a collect ambient sound; utilizing information of a phoneme or syllable contained in the audio signal to output time information, the time information identifying a point in time of uttering the phoneme or syllable;

receiving a measured electroencephalogram signal of a user; determining a difficulty of hearing of the phoneme or syllable by relying on an event-related potential based on the identified point of uttering the phoneme or syllable as a starting point, the event-related potential being acquired from the electroencephalogram signal;

when a plurality of phonemes or syllables are determined as difficult to hear in the determination step, identifying a phoneme or syllable closest to a beginning among the plurality of phonemes or syllables to be difficult to hear; and with respect to the identified phoneme or syllable, determining a gain adjustment method based on a type of the phoneme or syllable, and adjusting a gain for outputting an audio signal for the phoneme or syllable based on the determined gain adjustment method.

* * * * *